United States Patent
Baker et al.

(10) Patent No.: US 12,329,398 B2
(45) Date of Patent: Jun. 17, 2025

(54) STONE FRAGMENT CAPTURE SYSTEMS FOR LITHOTRIPSY SYSTEMS

(71) Applicant: GYRUS ACMI, INC., Westborough, MA (US)

(72) Inventors: Charles A. Baker, Rogers, MN (US); David Bloem, Maple Grove, MN (US); Richard M. Braga, North Easton, MA (US); Arthur J. Bertelson, Buffalo, MN (US); Brian Schneider, Natick, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/417,387

(22) Filed: Jan. 19, 2024

(65) Prior Publication Data

US 2024/0148394 A1 May 9, 2024

Related U.S. Application Data

(63) Continuation of application No. 17/400,499, filed on Aug. 12, 2021, now Pat. No. 11,911,053.

(Continued)

(51) Int. Cl.
*A61B 17/22* (2006.01)
*A61M 1/00* (2006.01)
(Continued)

(52) U.S. Cl.
CPC ............. *A61B 17/22* (2013.01); *A61M 1/60* (2021.05); *A61M 1/79* (2021.05); *A61M 39/06* (2013.01);
(Continued)

(58) Field of Classification Search
CPC .......... A61B 17/22; A61B 2017/22014; A61B 2017/22079; A61B 2217/005; A61M 1/60;
(Continued)

(56) References Cited

U.S. PATENT DOCUMENTS

| | | | | |
|---|---|---|---|---|
| 4,655,754 A | * | 4/1987 | Richmond | A61M 1/60 604/323 |
| 4,750,488 A | | 6/1988 | Wuchinich et al. | |

(Continued)

FOREIGN PATENT DOCUMENTS

| | | |
|---|---|---|
| CN | 211132596 U | 7/2020 |
| CN | 116249495 A | 6/2023 |

(Continued)

OTHER PUBLICATIONS

"U.S. Appl. No. 17/400,499, Corrected Notice of Allowability mailed Jan. 30, 2024", 3 pgs.

(Continued)

*Primary Examiner* — Julian W Woo
(74) *Attorney, Agent, or Firm* — Schwegman Lundberg & Woessner, P.A.

(57) ABSTRACT

A lithotripsy device can comprise a handpiece, a lithotripsy probe extending from the handpiece, an energization source configured to deliver an energy to a distal end of the lithotripsy probe, a suction passage extending from the distal end of the probe and through the handpiece, and a capture device comprising a container comprising a storage space, an entry port configured to couple to the handpiece at the suction passage, and an exit port, and a capture element connected to the container and configured to facilitate capture of stone fragments within the storage space. A method can comprise fragmenting stones with a lithotripsy device, drawing a vacuum through the lithotripsy device to pull (Continued)

stone fragments and waste fluid therethrough, pulling the vacuum through a stone capture device connected to the lithotripsy device, depositing stone fragments within the stone capture device using a capture element, and drawing the vacuum through the device.

32 Claims, 13 Drawing Sheets

Related U.S. Application Data

(60) Provisional application No. 63/065,958, filed on Aug. 14, 2020.

(51) Int. Cl.
*A61M 39/06* (2006.01)
*A61M 39/12* (2006.01)
*A61B 17/00* (2006.01)

(52) U.S. Cl.
CPC ..... *A61M 39/12* (2013.01); *A61B 2017/0034* (2013.01); *A61B 2017/22014* (2013.01); *A61B 2017/22079* (2013.01); *A61B 2217/005* (2013.01); *A61M 2039/0666* (2013.01)

(58) Field of Classification Search
CPC . A61M 1/79; A61M 39/12; A61M 2039/0666
See application file for complete search history.

(56) References Cited

U.S. PATENT DOCUMENTS

| | | | |
|---|---|---|---|
| 5,766,134 | A | 6/1998 | Lisak et al. |
| 6,375,651 | B2 | 4/2002 | Grasso, III et al. |
| 6,733,664 | B2 * | 5/2004 | Menne .............. A61M 1/60 210/438 |
| 8,100,892 | B2 * | 1/2012 | Liu ................ A61B 18/245 606/2.5 |
| 9,421,023 | B2 | 8/2016 | Bond et al. |
| 9,974,552 | B2 | 5/2018 | St. George et al. |
| 10,933,176 | B2 | 3/2021 | Gavlak et al. |
| 11,241,243 | B2 | 2/2022 | Pereira et al. |
| 11,911,053 | B2 | 2/2024 | Baker et al. |
| 2004/0077993 | A1 | 4/2004 | Cionni |
| 2005/0139532 | A1 | 6/2005 | Hershberger et al. |
| 2010/0185150 | A1 | 7/2010 | Zacharias |
| 2010/0297577 | A1 | 11/2010 | Cohen |
| 2011/0160620 | A1 | 6/2011 | Gill et al. |
| 2013/0345652 | A1 * | 12/2013 | Murray ............... A61M 1/743 210/136 |
| 2014/0336599 | A1 * | 11/2014 | Patel .............. A61M 1/79 604/319 |
| 2018/0280047 | A1 | 10/2018 | Ripich et al. |
| 2019/0133615 | A1 | 5/2019 | Pereira et al. |
| 2019/0201594 | A1 | 7/2019 | Shelton, IV et al. |
| 2021/0316127 | A1 | 10/2021 | Buck et al. |
| 2022/0047283 | A1 | 2/2022 | Baker et al. |

FOREIGN PATENT DOCUMENTS

| | | |
|---|---|---|
| DE | 112021004297 T5 | 7/2023 |
| JP | S63500850 A | 3/1988 |
| JP | H0151232 B2 | 11/1989 |
| JP | H02141425 A | 5/1990 |
| JP | H05285148 A | 11/1993 |
| JP | 2004525657 A | 8/2004 |
| JP | 2016059710 A | 4/2016 |
| WO | WO-2019152727 A1 | 8/2019 |
| WO | WO-2019239375 A2 | 12/2019 |
| WO | WO-2022036038 A1 | 2/2022 |

OTHER PUBLICATIONS

"U.S. Appl. No. 17/400,499, Corrected Notice of Allowability mailed Nov. 14, 2023", 3 pgs.
"U.S. Appl. No. 17/400,499, Examiner Interview Summary mailed Sep. 18, 2023", 2 pgs.
"U.S. Appl. No. 17/400,499, Final Office Action mailed Aug. 11, 2023", 14 pgs.
"U.S. Appl. No. 17/400,499, Non Final Office Action mailed Apr. 14, 2023", 11 pgs.
"U.S. Appl. No. 17/400,499, Notice of Allowance mailed Oct. 25, 2023", 9 pgs.
"U.S. Appl. No. 17/400,499, Preliminary Amendment filed Aug. 12, 2021", 6 pgs.
"U.S. Appl. No. 17/400,499, Response filed Jul. 14, 2023 to Non Final Office Action mailed Apr. 14, 2023", 16 pgs.
"U.S. Appl. No. 17/400,499, Response filed Oct. 10, 2023 to Final Office Action mailed Aug. 11, 2023", 13 pgs.
"International Application Serial No. PCT/US2021/045664, International Preliminary Report on Patentability mailed Feb. 23, 2023", 8 pgs.
"International Application Serial No. PCT/US2021/045664, International Search Report mailed Nov. 2, 2021", 7 pgs.
"International Application Serial No. PCT/US2021/045664, Written Opinion mailed Nov. 20, 2021", 6 pgs.
"Japanese Application Serial No. 2023-510429, Final Notification of Reasons for Rejection mailed Apr. 30, 2024", w/ English translation, 6 pgs.
"Japanese Application Serial No. 2023-510429, Notification of Reasons for Refusal mailed Dec. 25, 2023", w/ English Translation, 18 pgs.
"Japanese Application Serial No. 2023-510429, Response filed Mar. 25, 2024 to Notification of Reasons for Refusal mailed Dec. 25, 2023", w/ english claims, 12 pgs.
"Japanese Application Serial No. 2023-510429, Notification of Reasons for Rejection mailed Oct. 15, 2024", W/English Translation, 8 pgs.
"Japanese Application Serial No. 2023-510429, Response filed Jul. 31, 2024 to Final Notification of Reasons for Rejection mailed Apr. 30, 2024", W/English Claims, 6 pgs.

* cited by examiner

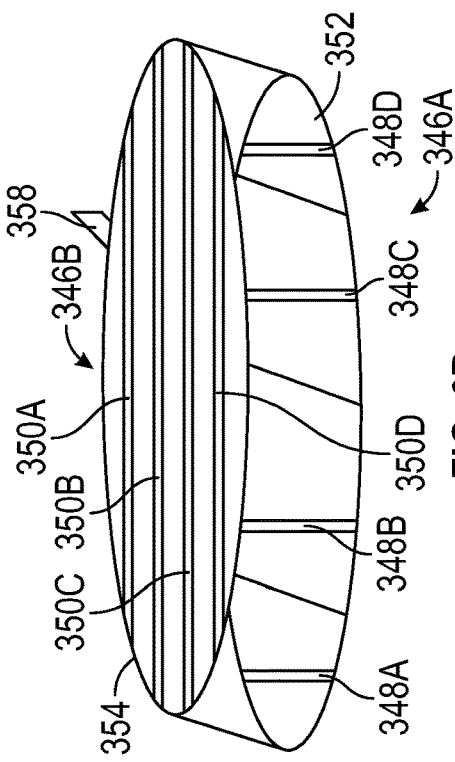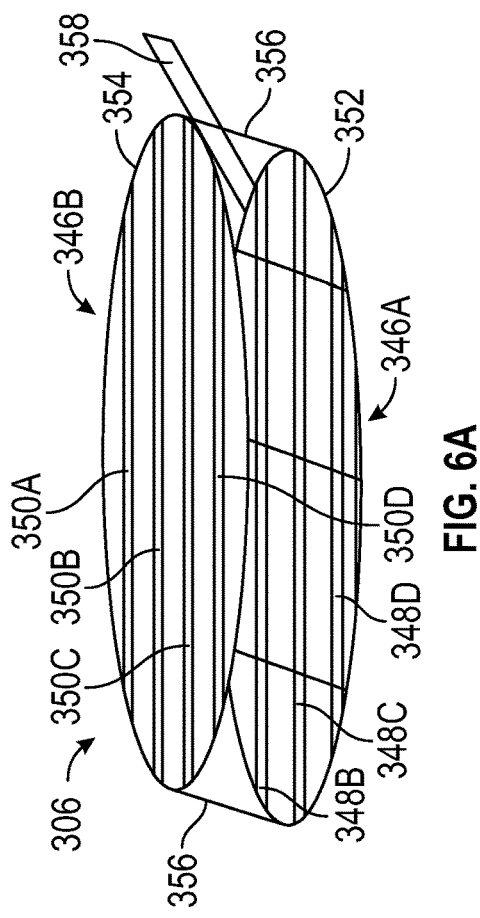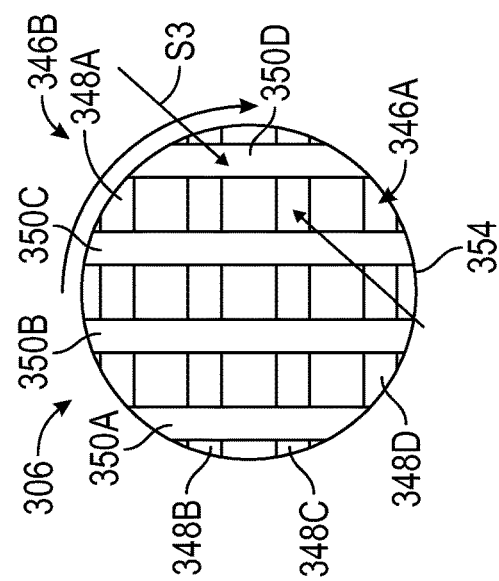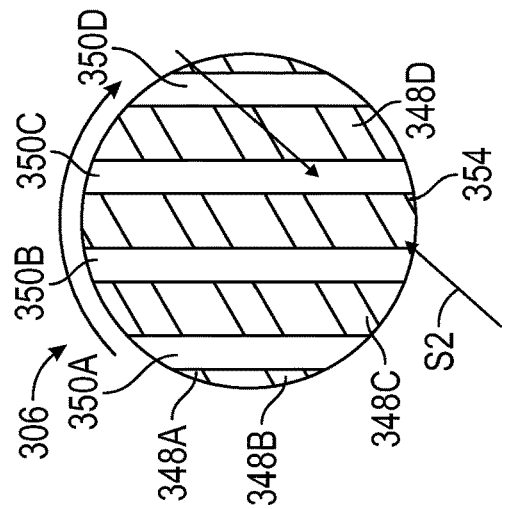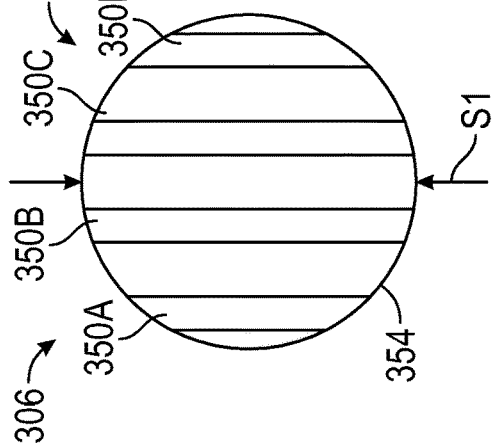

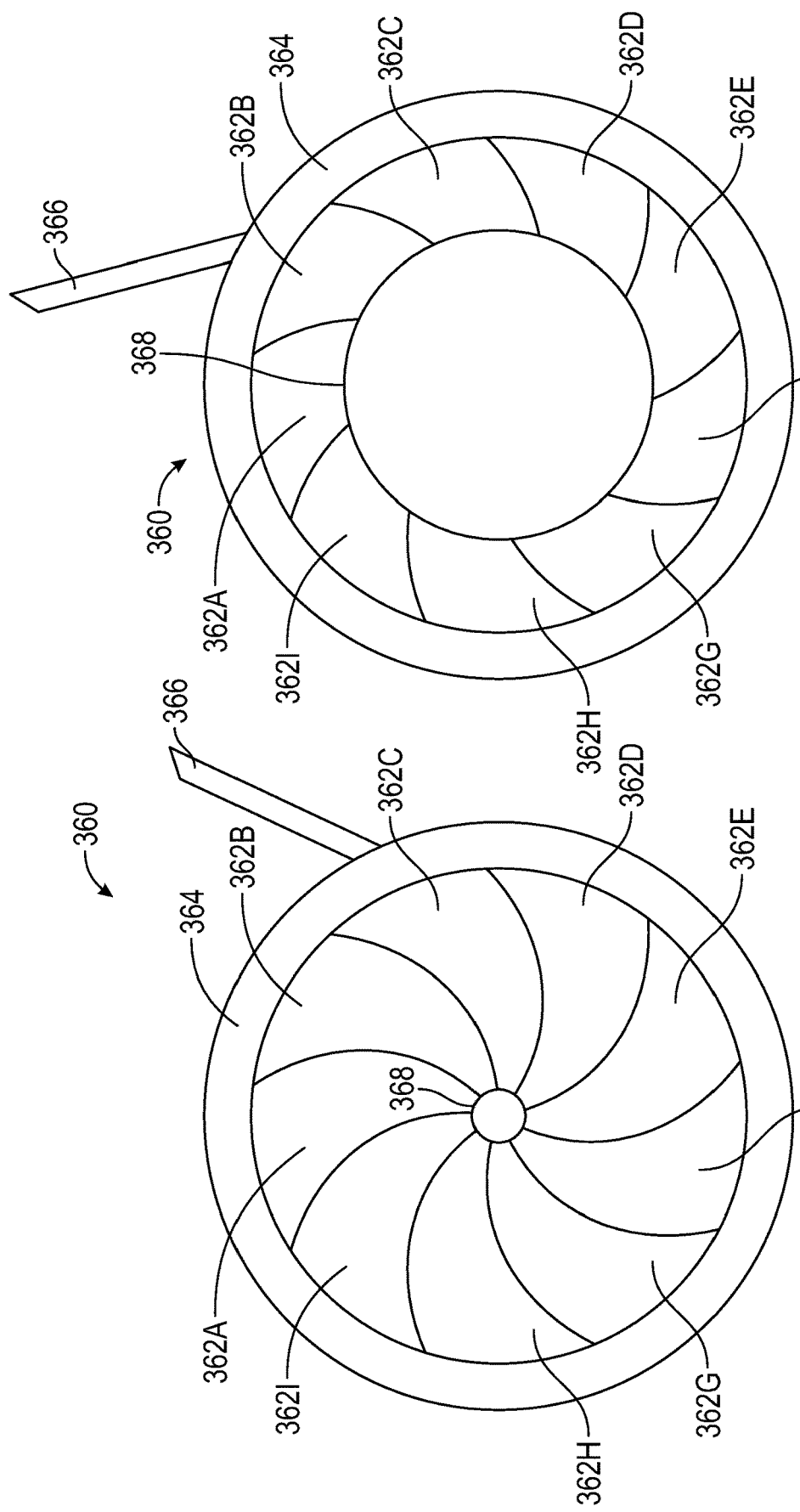

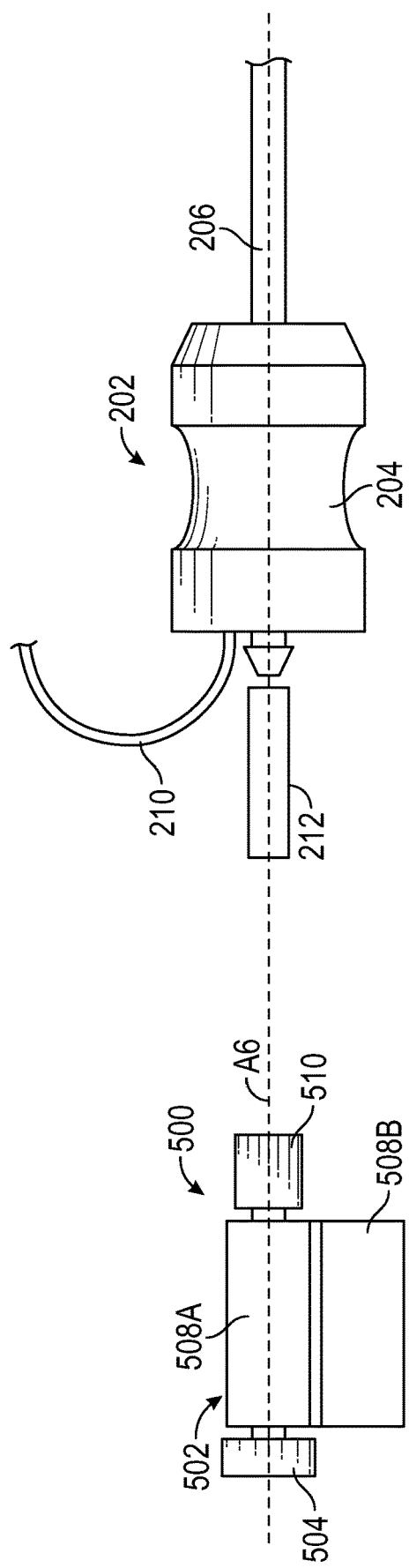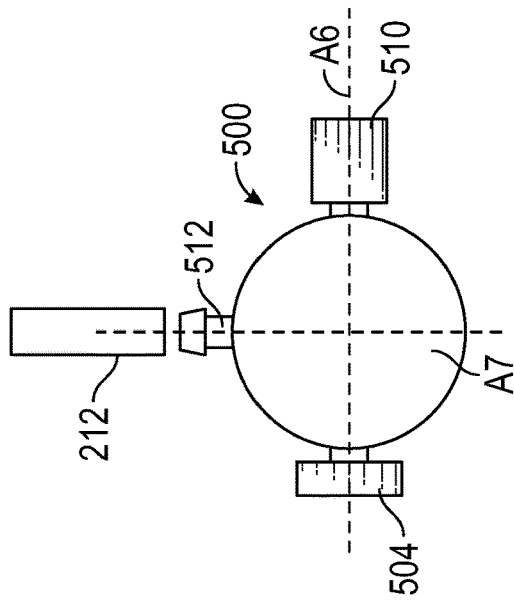
FIG. 15
FIG. 16

STONE FRAGMENT CAPTURE SYSTEMS FOR LITHOTRIPSY SYSTEMS

CROSS-REFERENCE TO RELATED APPLICATIONS

This application is a Continuation of U.S. patent application Ser. No. 17/400,499, filed Aug. 12, 2021, which claims the benefit of priority to U.S. Provisional Patent Application Ser. No. 63/065,958, filed Aug. 14, 2020, the contents of which are incorporated herein by reference in their entireties.

TECHNICAL FIELD

The present disclosure relates generally to medical devices that can be used to break obstructions, such as physiological calculi or "stones" using lithotripsy.

More specifically, the present disclosure relates to systems, devices and methods for capturing stone fragments from lithotripsy systems.

BACKGROUND

Medical endoscopes were first developed in the early 1800s and have been used to inspect inside the body. A typical endoscope includes a distal end comprising an optical or electronic imaging system and a proximal end with controls for manipulating the tools and devices for viewing the image, with a solid or tubular elongate shaft connecting the ends. Some endoscopes allow a physician to pass tools or treatments down one or more hollow working channels, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient to experience a substantial amount of pain. Therefore, these calculi are typically broken down for surgical removal or biological passing. Different techniques and procedures have been developed to break up stones, including ultrasonic lithotripsy, pneumatic lithotripsy, electro-hydraulic lithotripsy (EHL), and laser lithotripsy including dissolution of calculi using green light, YAG, or holmium lasers.

SUMMARY

The present inventors have recognized, among other things, that problems to be solved in performing lithotripsy procedures is the recovery of stone fragments from the patient during or after the procedure. Typically, stone fragments are removed from inside the patient via suction applied to a distal end of a lithotripsy device. The suction pulls the stone fragments proximally through a suction tube and, typically, deposits the fragments into a waste container, along with other fluids from the patient, such as biological fluid and lavage fluid. As such, stone fragments typically comprise part of a mixture of materials located in a single container, thereby making retrieval of the stone fragments difficult. Retrieval of stone fragments can be desirable so that analysis can be performed. For example, doctors can view the stone fragments to prescribe diets to prevent future formation of stones or the stone fragments can be sent off to a laboratory for detailed composition analysis.

The present subject matter can provide solutions to this problem and other problems by providing stone fragment capture systems that collect stone fragments separately from other collected material, such as waste fluids. The stone fragment capture systems of the present disclosure can retrieve stone fragments from the flow of material being removed from the patient via suction. The stone fragments can be retained in a container that can hold the fragments for later retrieval and analysis pre-separated from waste fluids. In examples, the stone fragments can be stored in a sealed container for shipment to a laboratory without needing user intervention or repackaging.

The present inventors have also recognized, among other things, that problems to be solved in performing lithotripsy procedures is the possibility of a lithotripsy device becoming clogged with stones or stone fragments. If such scenarios arise, it can result in interruption of the procedure so that the device can be disassembled to clear the blockage. For example, the system can be shut down and the device disconnected, disassembled, cleared and reassembled, thereby resulting in increased frustration and length of the procedure, as well as associated costs of extended procedure times.

The present subject matter can provide solutions to this problem and other problems by providing a vacuum port on an attachment for a lithotripsy device that can permit clearing of a blockage within the lithotripsy device without disassembly of the lithotripsy device or shutting down of the lithotripsy system. The vacuum port can provide a sealable access port into the lithotripsy device to allow insertion of an instrument to clear the blockage without interruption of the lithotripsy system, thereby reducing downtime and frustration associated with disassembly and reassembly. In examples, the vacuum port attachment can be integrated into a stone fragment capture system.

In an example, a lithotripsy device can comprise a handpiece, a lithotripsy probe extending from the handpiece, an energization source coupled to the handpiece configured to deliver an energy to a distal end of the lithotripsy probe, a suction passage extending from the distal end of the probe and through the handpiece, and a capture device coupled to the handpiece that can comprise a container comprising a storage space within the container, an entry port configured to couple to the handpiece at the suction passage, and an exit port, and a capture element connected to the container and configured to facilitate capture of stone fragments within the storage space.

In another example, a method of retrieving stone fragments from a lithotripsy procedure can comprise fragmenting stones with a lithotripsy device, drawing a vacuum through the lithotripsy device to pull stone fragments and waste fluid through the lithotripsy device, pulling the vacuum through a stone capture device connected to the lithotripsy device, depositing stone fragments within the stone capture device using a capture element, and continuing to draw the vacuum to deposit the waste fluid in a waste container.

In an additional example, a capture device for collecting fragments generated during lithotripsy can comprise a container comprising a wall defining a storage space within the container, an entry port coupled to the wall and configured to couple to the handpiece at the suction passage, and an exit port coupled to the wall, a capture element connected to the container and configured to facilitate capture of stone fragments within the storage space, and a coupler for connecting the container to a handpiece of a lithotripsy device.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIGS. 6A and 6B are schematic perspective views of a flow-restricting valve comprising an adjustable mesh valve suitable for use with the stone fragment capture system of FIG. 5.

FIGS. 7A-7C comprise schematic top views of the adjustable mesh valve of FIGS. 6A and 6B in large, medium and small opening configurations, respectively.

FIGS. 8A and 8B are schematic top views of a flow-restricting valve comprising an iris valve in closed and open configurations, respectively, suitable for use with the stone fragment capture system of FIG. 5.

FIG. 15 is a schematic cross-sectional view of a fourth example of a stone fragment capture system comprising a stone capture with a vacuum port for use with a stone fragmentation system, such as the lithotripsy systems described herein.

FIG. 16 is a schematic top view of the stone capture of FIG. 15 showing a position of an outlet relative to an inlet and the vacuum port.

Figure 1:
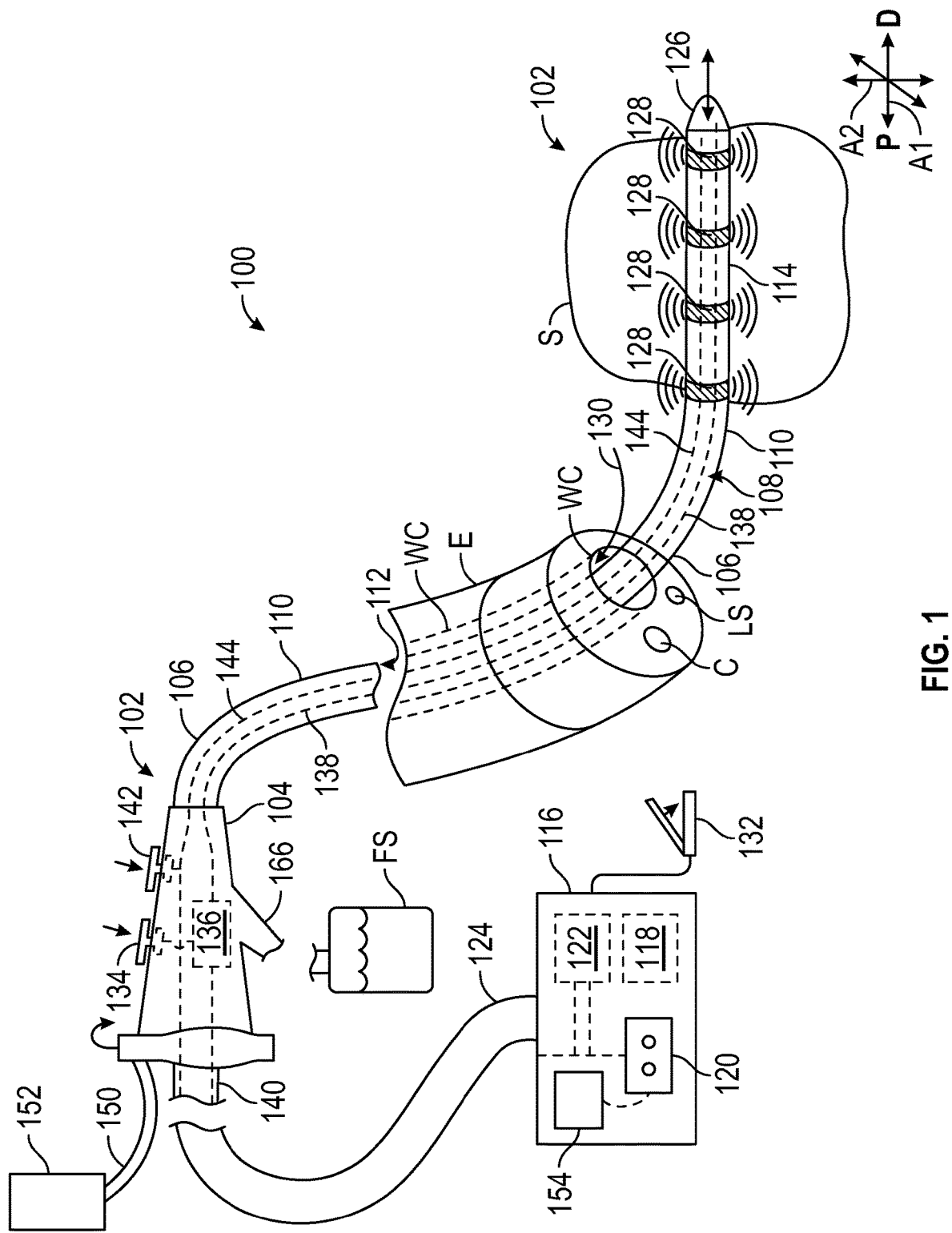
FIG. 1 is an isometric view of an illustration of an exemplary lithotripsy system with which the various stone fragment capture devices and systems of the present disclosure can be used.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides examples of devices, systems and methods that can help address problems associated with fragmenting stones and collecting stone fragments during lithotripsy procedures. In particular, the present disclosure provides examples of devices, systems and methods that can be used to retrieve stone fragments from the collection process for later analysis. Typically, collection of stone fragments for later analysis can be challenging due to the stone fragments being simultaneously collected with other fluids of the procedure, thereby requiring subsequent processing, such as separating and repackaging. Benefits of the approaches described herein include, among other things, capturing stone fragments in a container separately from waste fluid, thereby reducing post-processing procedures and times. The stone fragments can thus be pre-separated from the waste fluid and stored in a container that can be used to store or ship the stone fragments. Furthermore, the stone fragment capture devices described herein can include a vacuum port that allows access for unclogging of a lithotripsy device without the need for disassembly of the lithotripsy device.

FIG. 1 illustrates an isometric view of an example of lithotripsy system 100 including lithotripter 102 having housing 104, such as a handle. Lithotripter 102 can include delivery member 106 that is deliverable to a treatment site through working channel WC of endoscope E. Endoscope E can also include light source LS and camera C.

Delivery member 106 can include flexible or rigid elongate shaft 108 having a tubular structure. Suitable materials for the delivery member include, but are not limited to, polytetrafluoroethylene ("PTFE"), polyethylenes ("PE") and polyamides. Elongate shaft 108 can include outer surface 110 and at least one lumen 112 extending therethrough, the lumen being suitable for passage of components and materials that communicate with end effectors described herein.

Delivery member 106 can include an end effector such as probe 114 at a distal end that is deliverable to a treatment site. Probe 114 can be configured to deliver energy to fragment a mobile calculus such as a stone located in a bile duct, urinary tract, kidney or gall bladder. Probe 114 of lithotripter 102 can be introduced into a patient, driven by delivery member 106 through working channel WC of endoscope E or similar instrument. Probe 114 can be flexible or rigid.

Lithotripter 102 can be connected to signal generator 116. Signal generator 116 can include power source 118 or can be couplable to an external power source. Signal generator 116 can also include input 120 to receive an instruction from an operator, and may include controller 122 having processing circuitry for determining actions based on operator input and for sending control signals via output 124 for communication to lithotripter 102. Signal generator 116 can produce signals and send them to probe 114 of lithotripter 102 to cause probe 114 to emit acoustic energy. Acoustic energy can include sound waves, sonic waves, ultrasonic waves or shock waves, or any combination of these. Acoustic energy can be delivered to stone S to deteriorate, crack and thereby fracture stone S. The examples herein are described with reference to combinations of ultrasonic and shock wave applications but any suitable acoustic energy, or combinations thereof, for fracturing stones can be provided. The terms sonic and ultrasonic may be used herein interchangeably, and can include any suitable acoustic energy for fragmenting stones.

Features of probe 114 can provide improved fragmenting of stone S. For example, probe 114 can include drill 126 (which need not include a rotating drill bit), such as an ultrasonic drill that emits acoustic energy, in longitudinal direction A1, to drill a hole in the stone. Probe 114 can also include one or more lateral emitters 128 such as a lateral ultrasonic transducer to deliver acoustic energy inside the hole to fragment the stone from the inside out.

Drill 126 can be coupled to elongate shaft 108 and can be located at a distal tip of probe 114. Drill 126 can include at least a portion that extends distal of elongate shaft 108. In the example of FIG. 1, drill 126 can be configured to emit ultrasonic energy in longitudinal direction A1. Drill 126 can cause mechanical modification or destruction of stone S by producing pulsatile shock waves that move generally along longitudinal direction A1. Drill 126 can be configured to drill a hole, such as a recess into, or passage P through, stone S. FIG. 1 shows an example including drill 126 that has drilled passage P through stone S.

Drill 126 can be an ultrasonic emitter that receives ultrasonic energy from remotely located ultrasonic transducer 136, which will be referred to as drill transducer 136 for the purposes of clarity over other emitters and transducers in this disclosure. Drill transducer 136 can be located, for example, in housing 104 of lithotripter 102. Drill transducer 136 can transmit ultrasonic energy in generally longitudinal direction A1, distally out of housing 104. Ultrasonic energy can be transmitted from drill transducer 136 to drill 126 via ultrasound transmission member 138. Ultrasound transmission member 138 can be coupled to drill transducer 136 at a proximal end and to drill 126 at the distal end. Ultrasound transmission member 138 can be formed of any material that is capable of transmitting the ultrasound energy from drill transducer 136 to drill 126, including but not limited to metal, metal alloys, shape memory alloys, polymers, ceramics, fibers, crystals or composites thereof.

Drill transducer 136 can be electrically couplable to signal generator 116, such as by connector 140, to receive signals for operating drill 126. Drill transducer 136 can be actuated by, for example, an operator depressing foot pedal 132 that is in electrical communication with signal generator 116, or can be actuated by drill actuator 134 coupled to housing 104 that is in electrical communication with signal generator 116. Additionally or alternatively, the drill transducer 136 may be operated based on the input 120 from the operator and/or the actions determined by the controller 122. Any other suitable actuator for controlling activation of drill 126 can be provided.

Although drill 126 is described as an ultrasonic drill, in some examples, other types of drills may be provided, including but not limited to, a rotational drill operated by a motor. Like the drill transducer in the example of FIG. 1, the motor can be located remotely of probe 114, such as in housing 104, and the motor can be coupled to drill 126 via a rotational transmission member. In other words, in a variation on the example of FIG. 1, a rotational motor can be provided in place of drill transducer 136, and a rotational transmission member can be provided in place of ultrasound transmission member 138.

In addition to using an ultrasonic emitter for drilling, probe 114 can include at least one radial or lateral ultrasonic emitter 128 configured to direct ultrasonic energy in radial or lateral direction A2, outward and away from longitudinal direction A1 such as toward an internal surface (passage P) of stone S. In the example of FIG. 1, the at least one lateral ultrasonic emitter 128 includes a plurality or array of lateral ultrasonic emitters 128.

Each of lateral ultrasonic emitters 128 can direct ultrasonic energy in lateral direction A2, with each of lateral ultrasonic emitters 128 located along a different longitudinal position on probe 114. In some examples lateral ultrasonic emitters 128 can be spaced apart along longitudinal direction A1. Lateral ultrasonic emitters 128 can extend laterally or radially around probe 114. In some examples, lateral ultrasonic emitters 128 can extend around the entire three-hundred-sixty degree circumference of probe 114, or around a perimeter of probe 114 when a probe has a non-circular cross-section in direction lateral or perpendicular A1 to longitudinal direction A1. In other examples, lateral ultrasonic emitters 128 can only partially wrap around probe 114.

Lateral ultrasonic emitters 128 can be located proximal of drill 126. A benefit of this arrangement is that lateral ultrasonic emitter 128 can follow drill 126 so that after drill 126 prepares the passage P in stone S, lateral sonic emitter 128 can be advanced through passage P. When activated, such as by lateral emitter actuator 142 that is in electrical communication with lateral ultrasonic emitters 128 via electrical element 144 such as a wire, lateral ultrasonic emitters 128 can be configured to emit ultrasonic energy into to passage P and internal to stone S to fracture stone S from the inside of stone S.

Similar to drill transducer 136, lateral ultrasonic emitter 128 can include an ultrasonic or other acoustic transducer. An electrical-to-acoustic transducer is a component that can convert an electrical signal into variations in a physical quantity such as sound waves or pressure. Ultrasonic transducers can include linear piezoelectric stacks having piezoelectric elements located between two metal plates. In additional examples, magneto-restrictive stacks can be used. Such piezoelectric elements can convert electrical energy (e.g., electric current) into mechanical energy (e.g., sound waves, sonic waves, ultrasonic waves, shock waves). Piezoelectric elements can include crystal, such as quartz, having physical characteristics that results in the crystal undergoing mechanical stress when subjected to an electric field that causes the crystal to change size or shape. The piezoelectric elements or alternatively expand and contract in response to an alternating electric field, such as can be supplied by signal generator 116. This expansion and contraction can generate sound waves that can be delivered to stone S to fracture stone S.

To help locate stone S relatively stationary relative to working channel WC of endoscope E while drilling the hole, and relatively stationary to probe 114 (except for longitudinal A1 movement of probe 114 through the stone), suction, as denoted by suction arrow 130, can be applied through working channel WC. Suction 130 can cause Stone S to be "captured" by pulling stone S towards working channel WC and thus pulling stone S towards drill 126 of probe 114 for drilling Upon fracturing of stone S, stone fragments can be suctioned into working channel WC.

Some lithotripsy systems described herein can include fluid input 166 for receiving fluid from fluid storage FS and delivering fluid to a treatment site. For example, irrigation fluid or lavage fluid can be transmitted through endoscope E or elongate shaft 108. Typical stone fragment recovery systems involve simply collecting a mixture of solids and liquids retrieved from the patient while performing the procedure. For example, suction 130 can be applied at distal end of endoscope E or elongate shaft 108, and a vacuum drawn therethrough to deposit, materials, e.g., stone fragments and waste fluid, into a waste container. In examples, tube 150 can be connected to housing 104 to fluidly couple a lumen extending through working channel WC of endoscope E with collection container 152. Tube 150 can additionally be connected to suction device 154 or a pump to draw a vacuum through working channel WC, indicated with suction arrow 130.

Figure 2:
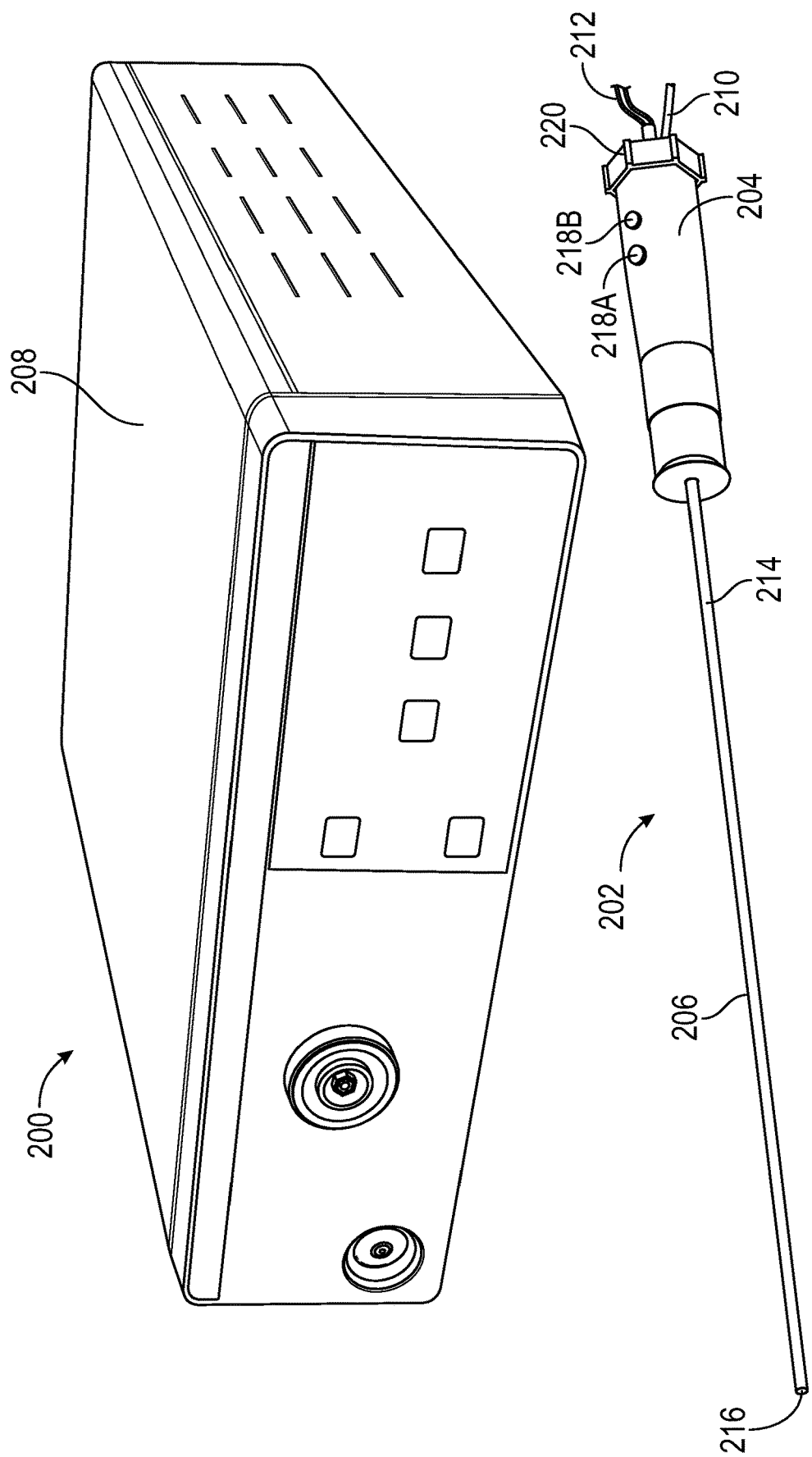
FIG. 2 is a perspective view of a lithotripsy system comprising a hand-held probe configured to deliver high frequency and ultrasonic energy for the fragmentation of stones.

FIG. 2 is a perspective view of lithotripsy system 200 comprising hand-held probe 202 configured to deliver high frequency and ultrasonic energy for the fragmentation of stones. In examples, lithotripsy system 200 can comprise an oscillating lithotripter as is described in Pat. No. U.S. Pat. No. 9,974,552 to St. George et al. titled "Oscillating Lithotripter" and which is assigned to Gyrus ACMI, Inc., the contents of which is incorporated herein in its entirety.

Hand-held probe 202 can comprise handpiece or handle 204 and shaft 206. Hand-held probe 202 can be connected to generator 208, such as via cable 210. Collection tube 212 can be connected to a storage container, such as fluid storage FS (FIG. 1), to collect fluid and other biological material collected via shaft 206. Shaft 206 can extend from proximal end 214 to distal end 216 and can comprise an internal lumen (e.g., lumen 532 of FIG. 17). Handle 204 can further comprise buttons 218A and 218B to control activation energy and knob 220 to control suction level.

Handle 204 can comprise any device suitable for facilitating manipulation and operation of shaft 206. Handle 204 can be located at proximal end 214 of shaft 206 or another suitable location along shaft 206. In examples, handle 204 can comprise a pistol grip, a knob, a handlebar grip and the like. In addition to or alternatively to buttons 218A and 218B and knob 220, handle 204 can comprise one or more of buttons, triggers, levers, knobs, dials and the like for control of energy activation, suction, irrigation and the like In various examples, distal end 216 of shaft 206, or another suitable location along shaft 16, can include a surgical device, which can comprise a component or device for interacting with a patient, such as those configured to cut and cauterize tissue and/or produce a desired tissue effect of the patient. In examples, the surgical tool can comprise forceps, a cutting tool, an ablation electrode, a cryogenic needle or applicator, an ultrasonic probe tip and the like, and combinations thereof. As such, hand-held probe 202 can be provided with a linkage, such as a mechanical linkage to actuate forceps or a cutting tool, an electrical linkage to activate an ablation electrode, an acoustic linkage, a liquid conduit (e.g., for the delivery of cryogenic argon gas) and the like, and combinations thereof. In examples, the surgical device can be included on a device used in conjunction with hand-held probe 202. In additional examples, hand-held probe 202 can comprise, or can be combined with, a device for viewing the patient, such as optical devices including endoscopes (e.g., endoscope E, above) and fiberscopes.

Generator 208 can comprise a source of energy for hand-held probe 202. For example, generator 208 can be configured to provide electricity for performing ablation and cauterizing functions and/or ultrasonic energy for providing cutting, coagulating, fragmenting or other types of surgical functions. In examples, generator 208 can provide ultrasonic wave energy, while intermittent ballistic shockwave energy is provided via an oscillating free mass within handle 204.

Shaft 206 can comprise an elongate member configure to deliver energy for fragmenting stones into a patient. Shaft 206 can be rigid and formed from a metal or plastic material. In examples, shaft 206 can be sized for performing lithotripsy procedures in conjunction with an endoscope. As such, shaft 206 can be inserted into an incision in the epidermis of a patient, through a body cavity of the patient and into an organ. Thus, it is desirable for the diameter or cross-sectional shape of shaft 206 to be as small as possible to facilitate minimally invasive surgical procedures. However, shaft 206 can also incorporate a lumen (e.g., lumen 532 of FIG. 17) to allow for removal, e.g., via suction, of fragments of stones produced by the fragmentation energy. As such, the size of shaft 206 and a lumen extending therethrough must be balanced to allow for minimal invasiveness and adequate removal of stone fragments. For example, too small of a lumen can increase the time it takes to fragment the stones into suitably small pieces.

Lithotripsy 100 of FIG. 1 and lithotripsy system 200 of FIG. 2 are examples of lithotripsy system that can be used with the stone fragment capture devices, systems and methods described herein. For example, a stone fragment capture device can be connected to housing 104 and tube 150 to collect stone fragments retrieved by lithotripter 102 and to facilitate unclogging of blockages that might form in lithotripter 102. Likewise, a stone fragment capture device of the present disclosure can be connected to handle 204 and tube 212. Although the present application is described with reference to lithotripsy systems used for retrieval of stones, other types of surgical devices and endoscopy devices can be used with stone fragment capture systems and methods disclosed herein. For example, any surgical device that can be configured for insertion into a patient that involves retrieval of biological matter along with waste fluid via suction can benefit from the present disclosure, such as forceps intended to remove endometrial tissue from a uterus. Examples of surgical devices that can be used with the present disclosure can utilize various energy sources, such as laser energy, ultrasound energy, and the like, for cracking, fragmenting, and/or dusting particles, such as stones and other solid or rigid bodies, and can perform evacuation of such particles after being broken down, such as by using a vacuum that pulls solids, liquids and mixtures into a designated collection receptacle.

Figure 3:
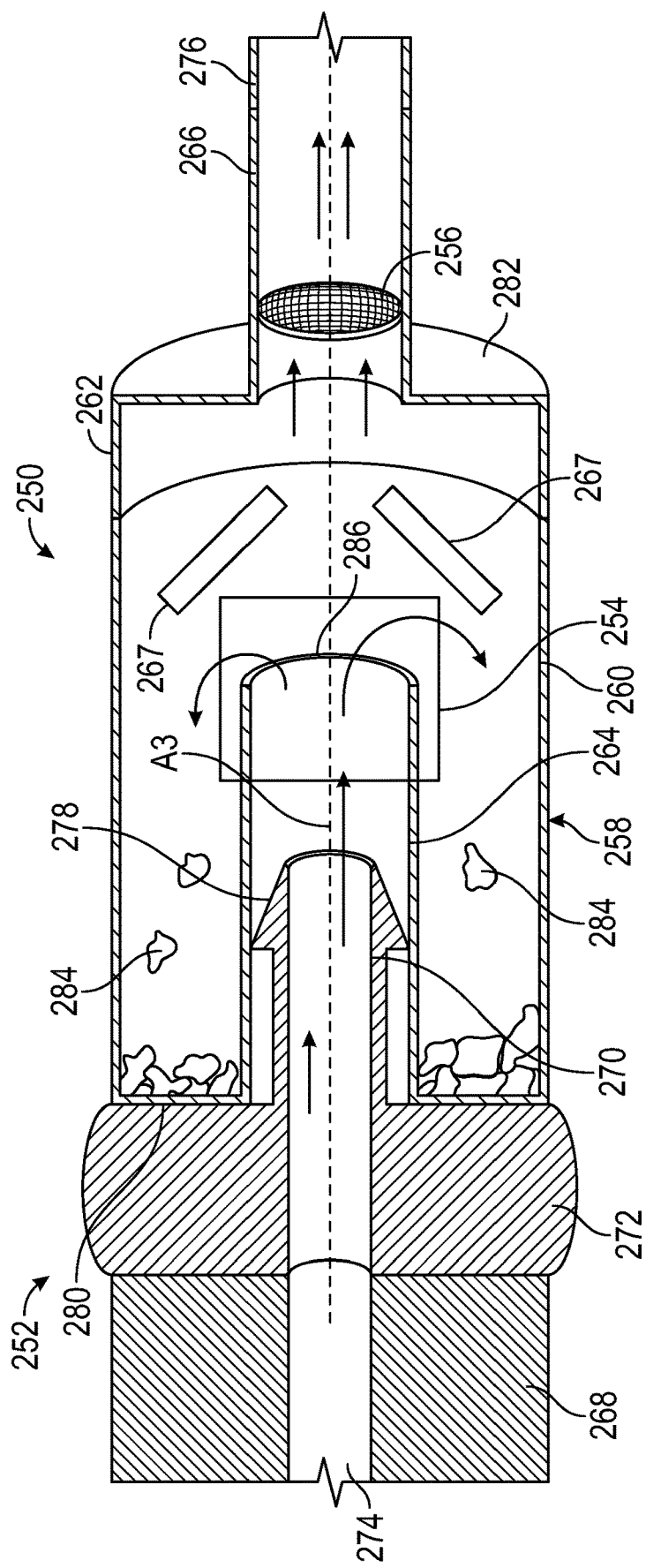
FIG. 3 is a schematic cross-sectional illustration of a first example of a stone fragment capture system comprising a valve and filter for use with a stone fragmentation system, such as the lithotripsy systems described herein.

FIG. 3 is a schematic cross-sectional illustration of stone fragment capture system 250 for use with stone fragmentation system 252 of FIG. 2. Stone fragmentation system 252 can be used with lithotripsy system 100 of FIG. 1 that can deliver fragmentation energy radially along probe 114, as well as stone lithotripsy system 200 of FIG. 2 that can deliver fragmentation energy longitudinally along shaft 206. Stone fragment capture system 250 can comprise valve 254 and filter 256, which can be coupled to container 258. Container 258 can comprise housing 260, cap 262, inlet port 264, outlet port 266 and baffles 267.

Stone fragmentation system 252 can comprise any of the lithotripsy systems described herein, or another surgical system configured to generate suction therethrough. Stone fragmentation system 252 can comprise handle 268 and stem 270. In examples, handle 268 can include knob 272 similar to knob 220 of FIG. 2 to control a function of stone fragmentation system 252, such as suction level. Passage 274 can be configured to extend from handle 268, such as from a shaft or probe extending distally therefrom, and through knob 272 and stem 270 located at a proximal end.

Container 258 can be coupled to handle 268 and tube 276. Housing 260 can be positioned such that inlet port 264 couples to stem 270. Stem 270 can comprise barb 278 that can be configured to facilitate attachment of container 258 to handle 268. For example, barb 278 can be a resilient rim extending around stem 270 that can have a diameter slightly larger than the inner diameter of stem inlet port 264. Inlet port 264 can comprise a cylindrical tube extending from floor 280 of housing 260. A tube forming inlet port 264 can be tapered to slow movement of fragments 284 entering container 258. Floor 280 can comprise an annular disk connecting inlet port 264 to housing 260. Likewise, outlet port 266 can comprise a cylindrical tube extending from cap 262. Cap 262 can comprise end plate 282, which can comprise an annular disk connecting outlet port 266 to cap 262. Cap 262 can be coupled to housing 260 via any suitable means, such as a threaded connection or a snap fit connection. In examples, tube 276 can be integral with outlet port 266, as illustrated. In other examples, tube 276 can be coupled to outlet port 266 via a barbed connection similar to barb 278. Although the illustrated example shows container 258 being coupled directly to stem 270 of handle 268, container 258 can additionally be coupled to handle 268 via a length of tubing that can couple around stem 270 and be inserted into inlet port 264, for example.

Container 258 can be positioned between handle 268 and tube 276 to capture stone fragments 284 leaving passage 274. Inlet port 264 can be configured to align with outlet port 266 along axis A3. However, in other examples, outlet port 266 can be offset from axis A3, as discussed below with reference to FIGS. 15 and 16. Stone fragments 284 can flow through passage 274 from handle 268 to stem 270. Stone fragments 284 can be dispersed into the interior of container 258, such as by using a capture element comprising one or more of a tube comprising inlet port 264, baffles 267 and filter 256. For example, stone fragments 284 can fall via gravity to floor 280. In examples, housing 260 can extend beyond tip 286 of inlet port 264 to provide clearance for stone fragments 284 to enter container 258. In examples, end plate 282 can be positioned a distance away from tip 286 to allow momentum of stone fragments 284 to dissipate. Additionally, baffles 267 can be positioned opposite tip 286 to deflect fragments 284 into housing 260. Baffles 267 can comprise various shaped bodies extending radially inward from walls of housing 260 or axially outward from inlet port 264 to obstruct outlet port 266 from direct impingement of fragments 284. Baffles 267 can deaden the momentum of fragments 284 to facilitate movement of fragments 284 out of the suction path, e.g., path of flowing liquid, between inlet port 264 and outlet port 266.

Filter 256 can be positioned in container 258 to prevent egress of stone fragments 284 from container 258. In the illustrated example, filter 256 is positioned in outlet port 266. However, filter 256 can be positioned anywhere in container 258 to block free entry of material into outlet port 266. In examples, filter 256 can be mounted to cap 262 to facilitate access of stone fragments 284 within container 258 when cap 262 is removed. However, filter 256 can be configured to itself be removable from housing 260 independent of cap 262. Filter 256 can be sized to permit liquid and small pieces of tissue or stone fragments and other debris to pass through container 258, but that prevents large pieces of matter to be retained within container 258. The capture elements described herein, filter 256 and other filter or orifice elements described herein (e.g., flow restricting valve 360 of FIGS. 8A and 8B) can be sized to retain pieces of matter or stone fragments that are suitable for further analysis, such as visual viewing for color and texture analysis.

Valve 254 can be positioned proximate tip 286 of stem 270 and can be used to intermittently close stem 270 to prevent egress of stone fragments 284 out of container 258. For example, when container 258 is removed from inlet port 264 and tube 276 is removed from cap 262, valve 254 can close to prevent stone fragments 284 from leaving container 258 at inlet port 264. Valve 254 can comprise any suitable device for allowing flow into housing 260 when container 258 is attached to stem 270 and preventing stone fragments from leaving housing 260 when container 258 is detached from handle 268. Valve 254 can be configured to be mechanically opened by engagement with stem 270 or by operation of a vacuum being pulled through container 258. As discussed with reference to FIGS. 4A and 4B, valve 254 can comprise a biased stop.

Figure 4A:
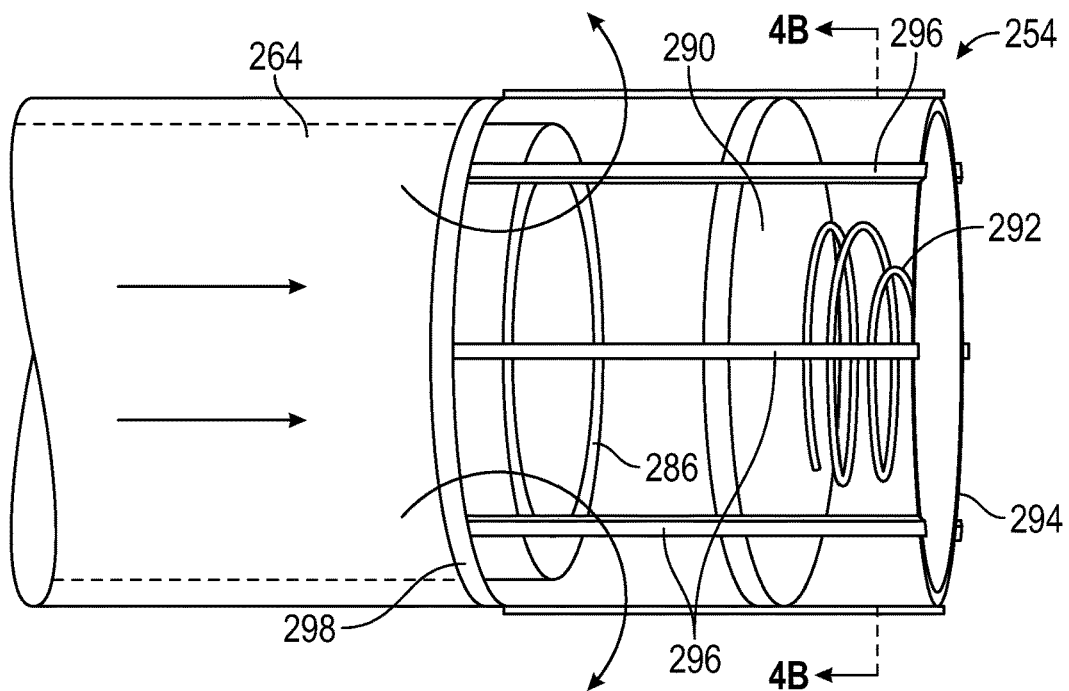
FIG. 4A is a side view of a valve for use with the stone fragment capture system of FIG. 3 comprising a biased stop.
Figure 4B:
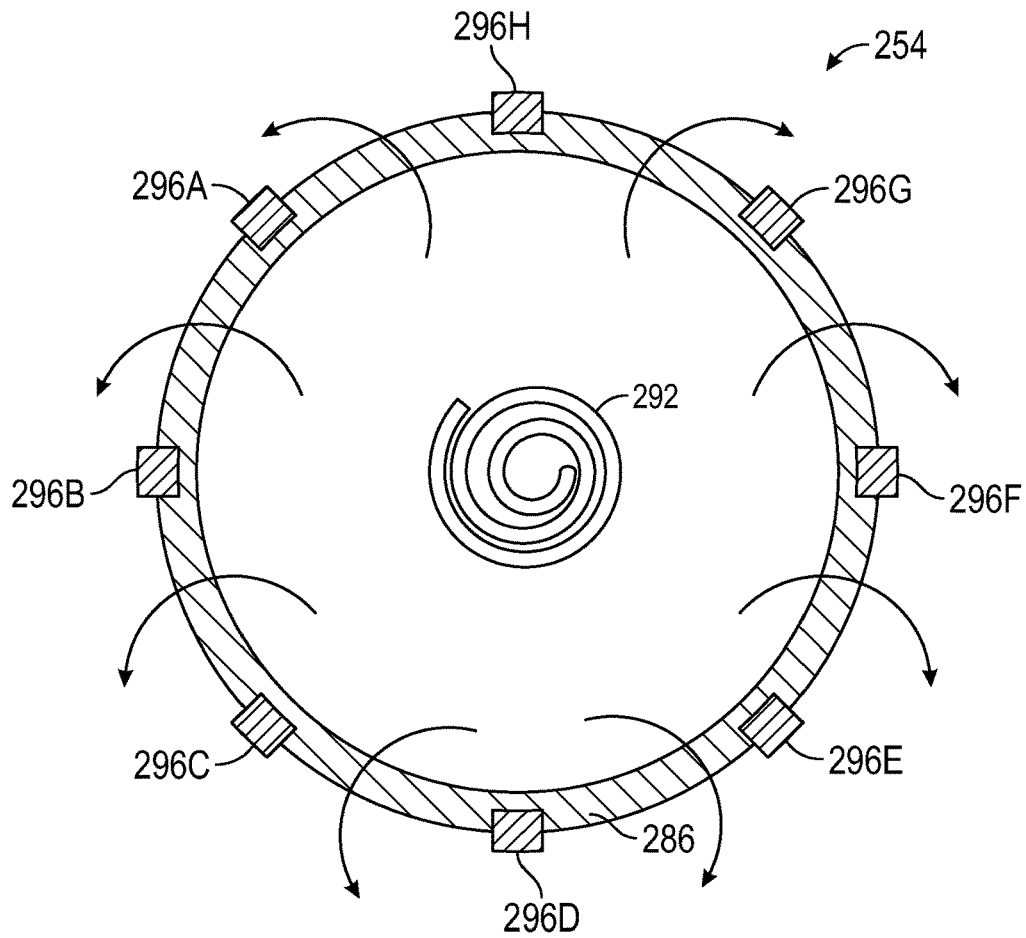
FIG. 4B is a cross-sectional view of the valve of FIG. 4A showing support struts for the biased stop with windows to allow for the passage of stones.

FIG. 4A is a side perspective view of a first example of valve 254 for use with stone fragment capture system 250 of FIG. 3. In the illustrated example, valve 254 can comprise stop 290, resilient element 292, backstop 294, struts 296A-296H and support ring 298. FIG. 4B is a cross-sectional view of valve 254 of FIG. 4A taken at section 4B-4B to show support struts 296A-296H. FIGS. 4A and 4B are discussed concurrently. Struts 296A-296H can be connected to ring 298 at a first end and back stop 294 at a second end. Support ring 298 can be positioned around stem 270 to position backstop 294 to oppose the opening of inlet port 264 connecting to passage 274. Support ring 298 can be coupled to inlet port 264 using any suitable means, such as adhesive, fasteners or threaded fastening. Struts 296A-296H can be used to guide stop 290 into engagement with and away from tip 286. Stop 290 can comprise a circular or rectangular shape, or any suitable shape to close of inlet port 264. Stop 290 can include bores or notches to slide along struts 296A-296H, or can simply be guided between struts 296A-296H. When stone fragmentation system 252 is not operating, resilient element 292 can push against backstop 294 to push stop 290 against inlet port 264. As such, egress and ingress of material into container 258 can be prevented or inhibited. When stone fragmentation system 252 is operating, a vacuum can be drawn from tube 276 to pull stop 290 away from tip 286. As such, stone fragments 284 can flow out of inlet port 264 and between struts 296A-296H to enter container 258.

Figure 5:
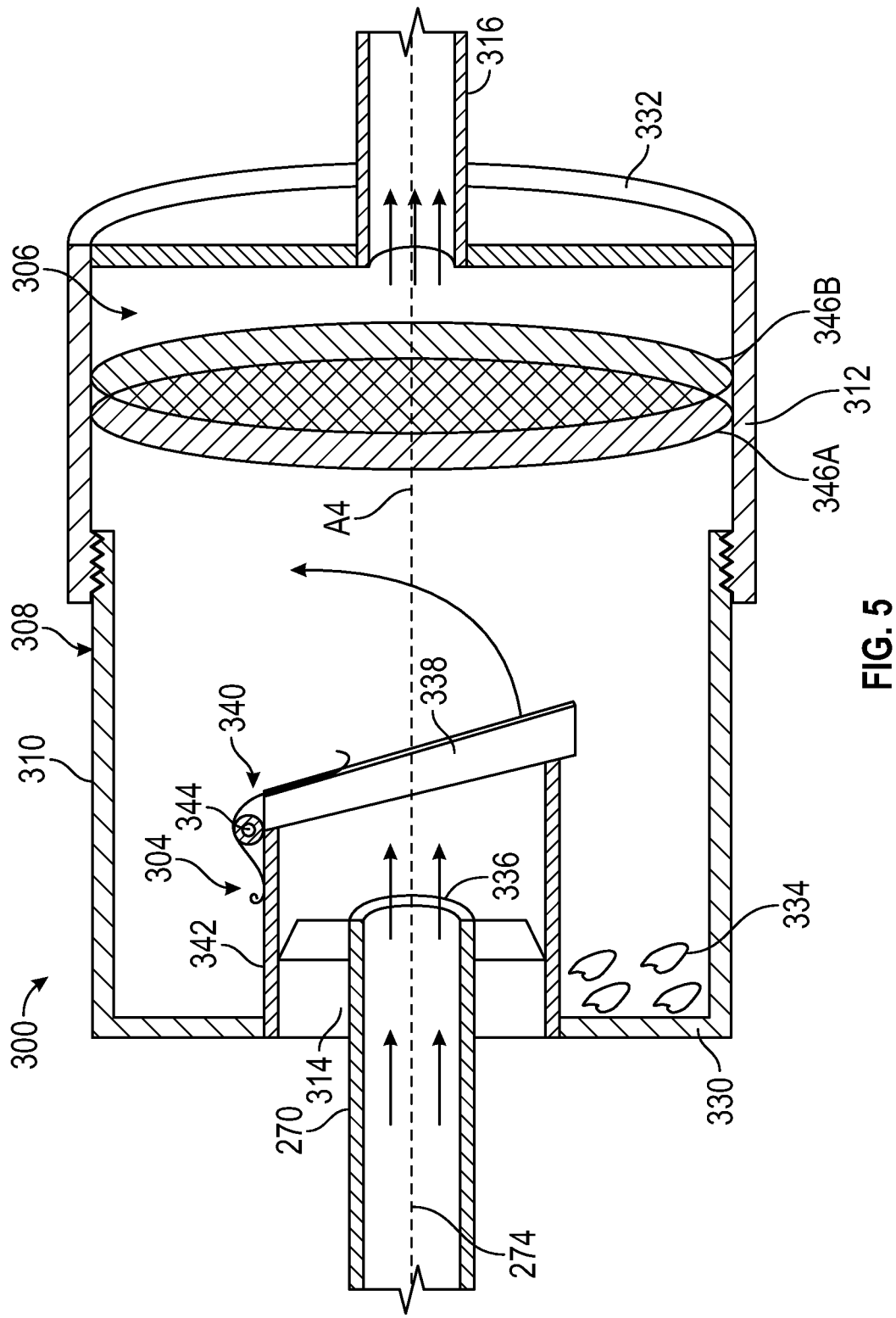
FIG. 5 is a schematic cross-sectional view of a second example of a stone fragment capture system comprising a flapper valve and a flow-restricting valve for use with a stone fragmentation system, such as the lithotripsy systems described herein.

FIG. 5 is a schematic cross-sectional illustration of stone fragment capture system 300 for use with stone fragmentation system 252. Stone fragment capture system 300 can comprise valve 304 and filter 306, which can be coupled to container 308. Container 308 can comprise housing 310, cap 312, inlet 314 and outlet 316.

Stone fragment capture system 300 can be used with stone fragmentations systems described herein, such as stone fragmentation system 252, as well as other lithotripsy systems or another surgical system configured to generate suction therethrough. For example, inlet 314 can be connected to stem 270 such that passage 274 can connect to the interior of housing 310.

Container 308 can be coupled to handle 268 (FIG. 3) and tube 276 (FIG. 3). Housing 310 can be positioned such that inlet 314 couples to stem 270. Inlet 314 can comprise a cylindrical opening extending through floor 330 of housing 310. Inlet 314 can comprise a resilient material having an opening slightly smaller than the diameter of stem 270 such that a tight, sealed fit can be achieved therebetween. Floor 330 can comprise an annular disk or polygonal plate connecting inlet 314 to housing 310. Likewise, outlet 316 can comprise a cylindrical tube extending from cap 312. Cap 312 can comprise end plate 332, which can comprise an annular disk connecting outlet 316 to cap 312. Cap 312 can be coupled to housing 310 via any suitable means, such as a threaded connection or a snap fit connection. In examples, tube 276 can be integral with outlet 316. In other examples, tube 276 (FIG. 3) can be coupled to outlet 316 via a barbed connection similar to barb 278 (FIG. 3). Although the illustrated example shows container 308 being coupled directly to stem 270 of handle 268, container 308 can be additionally be coupled to handle 268 via a length of tubing that can couple around stem 270 and be inserted into inlet 314, for example.

Container 308 can be positioned between handle 268 and tube 276 to capture stone fragments 334 leaving passage 274. Inlet 314 can be configured to align with outlet 316 along axis A4. However, in other examples, outlet 316 can be offset from axis A4, as discussed below with reference to FIGS. 15 and 16. Stone fragments 334 can flow through passage 274 from handle 268 to stem 270. Stone fragments 334 can be dispersed into the interior of container 308. For example, stone fragments 334 can fall via gravity to floor 330. In examples, housing 310 can extend beyond tip 336 of stem 270 to provide clearance for stone fragments 334 to enter container 308. In examples, end plate 332 can be positioned a distance away from tip 336 to allow momentum of stone fragments 334 to dissipate. Container 308 can be provided with capture elements as described with reference to FIG. 3, such as an elongate tube extending from inlet 314 and baffles similar to baffles 267.

Valve 304 can be positioned proximate tip 336 of stem 270 and can be used to intermittently close stem 270 to prevent egress of stone fragments 334 out of container 308. Valve 304 can comprise any suitable device for allowing flow into housing 310 when container 308 is attached to stem 270 and preventing stone fragments from leaving housing 310 when container 308 is detached from handle 268. In the illustrated embodiment, valve 304 can comprise a flapper valve having stop 338, resilient element 340 and sidewall 342. Sidewall 342 can comprise a cylindrical body or tube having another cross-sectional shape to circumscribe stem 270. Stop 338 can be pivotably coupled to sidewall 342 at coupling 344, which can comprise a pinned coupling. As such, stop 338 can rotate about coupling 344 between engaging sidewall 342 and being positioned approximately parallel to the central axis of stem 270. Resilient element 340 can bias stop 338 to a closed position in engagement with sidewall 342. Resilient element 340 can comprise a spring, such as a butterfly spring that can push against sidewall 342 and stop 338 simultaneously. Valve 304 can be configured to be opened upon flow of material through container 308, e.g., when a vacuum is pulled from outlet 316.

As discussed in greater detail with reference to FIG. 6A-7C, filter 306 can be positioned in container 308 to prevent egress of stone fragments 334 from container 308. Filter 306 can comprise a flow-restricting valve that can be adjusted to vary the size of stone fragments 334 that can be permitted to flow through stone fragment capture system 300. For example, filter 306 can comprise opposing mesh layers 346A and 346B, the relative positions of which can be varied to adjust radial gap sizes between the mesh.

FIGS. 6A and 6B are schematic perspective views of filter 306 comprising a flow-restricting valve suitable for use with stone fragment capture system 500 of FIG. 5, as well as other systems described herein. Filter 306 can comprise opposing mesh layers 346A and 346B. Mesh in each of layers 346A and 346B can be oriented parallel to each other. For example, layer 346A can include mesh strands 348A-348D, and layer 346B can comprise strands 350A-350D. Layers 346A and 346B are described as having four strands of parallel mesh each, but can include any suitable number of strands to filter or inhibit flow of biological material. Strands 348A-348D can be mounted to frame 352 and strands 350A-350D can be mounted to frame 354. Frames 352 and 354 can be connected by struts 356 such that frames 352 and 354 are rotatable relative to each other. One of frames 352 and 354 can be coupled to handle 358. As shown in FIG. 6A, strands 348A-348D and strands 350A-350D are parallel to each other in horizontal positions (relative to the orientation of FIG. 6A). In FIG. 6B, frame 352 is rotated relative to frame 354 by handle 358 in a counter-clockwise direction such that strands 350A-350D are in vertical positions (relative to the orientation of FIG. 6B) perpendicular to strands 348A-348D.

FIGS. 7A-7C comprise schematic top views of mesh layers 346A and 346B of filter 306 in aligned, transverse and perpendicular alignments, respectively. Accordingly, radial spacing between strands (relative to a center axis of frame 354, for example), such that strands 348A-348D and strands 350A-350D are arranged in large, medium and small spacing configurations.

In FIG. 7A, strands 348A-348D and strands 350A-350D are parallel to each other in vertical positions (relative to the orientation of FIG. 7A). As such, spacing S1, measured radially from the center of frame 354, is at its largest. In FIG. 7B, strands 3450A-350D are rotated approximately forty-five degrees clockwise relative to FIG. 7A. As such, spacing S2, measured radially from the center of frame 354, is smaller than S1.

In FIG. 7C, strands 3450A-350D are rotated approximately ninety degrees clockwise relative to FIG. 7A. As such, spacing S3, measured radially from the center of frame 354, is smaller than S2 and at its smallest.

Mesh layers 346A and 346B can be manually adjusted by a user of stone fragment capture system 500 to control the size of stone fragments desired to be captured by container 308. For example, mesh layers 346A and 346B can be adjusted to the position of FIG. 7A to collect large fragments, such as might be useful if only a few fragments are desired for laboratory analysis. However, mesh layers 346A and 346B can be adjusted to the position of FIG. 7C to collect only small fragments, such as might be useful if a large volume of fragments are desired for visual inspection.

FIGS. 8A and 8B are schematic top views of flow-restricting valve 360 suitable for use with stone fragment capture system 300 of FIG. 5. Flow-restricting valve 360 can comprise an iris valve having shims 362A-362G. FIG. 8A shows shims 362A-362G in a closed configuration and FIG. 8B shows 362A-362G in an open configuration. Shims 362A-362G can be bound by frame 364. Lever 366 can be connected to frame 364 to move shims 362A-362G between open and closed positions. As shown in FIG. 8A, shims 362A-362G can be positioned such that orifice 368 is small. Thus, flow-restricting valve 360 can be configured to minimize the amount of biological material that will pass through container 308, thereby decreasing the size of stone fragments that will be retained in container 308. As shown in FIG. 8B, shims 362A-362G can be positioned such that orifice 368 is large. Thus, flow-restricting valve 360 can be configured to maximize the amount of biological material that will pass through container 308, thereby increasing the size of stone fragments that will be retained in container 308. Thus, an operator of stone fragment capture system 500 of FIG. 5, for example, can tune flow-restricting valve 360 to the desired size of stone fragments to be retained by container 308. Shims 362A-362G can be configured to operate as would be appreciated by one of skill in the art, such as by being pinned at their outer diameter ends proximate frame 36 and being connected to an outer diameter actuation mechanism that simultaneously rotates each of shims 362A-362G at the pinned connection. In an example, flow-restricting valve 360 can be constructed similarly to an iris shutter similar to those used in cameras that is scaled-up in size and sturdiness for use in a pressurized environment as a flow control orifice.

Figure 9:
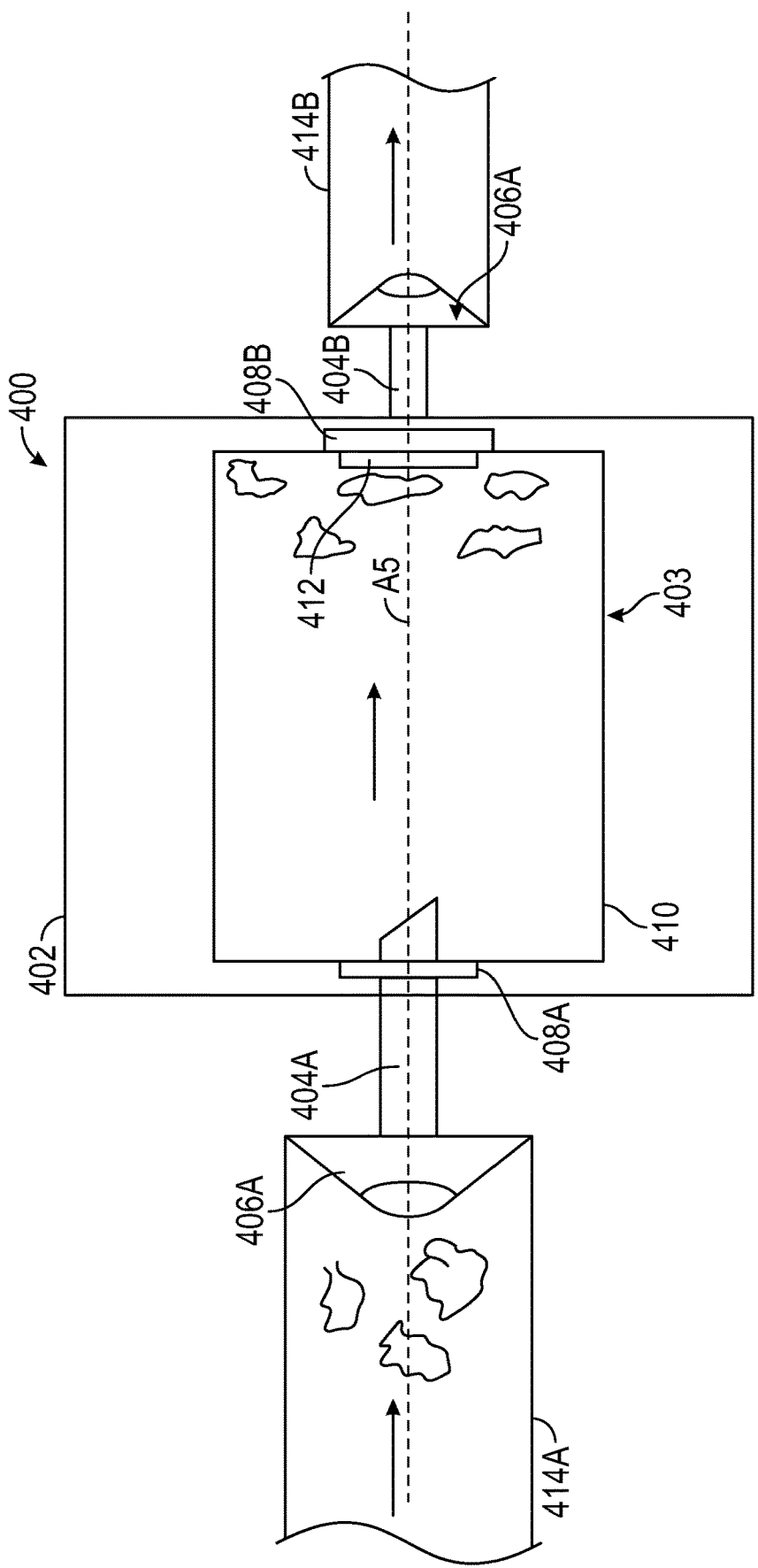
FIG. 9 is a schematic cross-sectional view of a third example of a stone fragment capture system comprising a cartridge and chassis assembly for use with a stone fragmentation system, such as the lithotripsy systems described herein.

FIG. 9 is a schematic cross-sectional illustration of stone fragment capture system 400 for use with stone fragmentation system 252, as well as other systems described herein. Stone fragment capture system 400 can comprise chassis 402 and cartridge 403. Chassis 402 can comprise stem 404A, stem 404B, barb 406A, barb 406B, first valve 408A and second valve 408B. Cartridge 403 can comprise housing 410 and filter 412.

Stone fragment capture system 400 can be coupled to tubes 414A and 414B. Stem 404A can be configured to align with stem 404B along axis A5. However, in other examples, stem 404B can be offset from axis A5, as discussed below with reference to FIGS. 15 and 16. Tube 414A can be connected to a fragmentation tool, such as handle 252. Tube 414B can be connected to a waste collection container and a vacuum generator, such as a pump.

Stone fragment capture system 300 can be used with stone fragmentations systems described herein, such as stone fragmentation system 252, as well as other lithotripsy systems. For example, inlet 314 can be connected to stem 270 such that passage 274 can connect to the interior of housing 310.

Stone fragment capture system 300 can be configured such that chassis 402 can remain connected to tubes 414A and 414B, while one or more cartridges 403 can be sequentially coupled to chassis 402. Additionally, each cartridge 403 can comprise a self-sealing system such that upon removal from chassis 402, each cartridge 403 is ready to be transported or shipped to a different location for storage and analysis. For example, valves 408A and 408B can be configured to open and close upon insertion and removal of cartridges 403 into chassis 402, as discussed with reference to FIGS. 11-14.

Chassis 402 and cartridge 403 can be configured for use with different system or to collect different sized stone fragments. For example, chassis 402 can include stems 404A and 404B with different sizes such that different sized tubes 414A and 414B can be connected thereto. Also, cartridge 403 can be configured to have different grade filters 412. Filter 412 can additionally comprise filter 306 of FIG. 5 or flow-restricting valve 360 of FIGS. 8A and 8B. As such, stone fragment capture system 300 can be configured to allow different size stone fragments to pass therethrough.

In examples, valves 408A and 408B can be attached to cartridge 403 and can be configured to open upon insertion of cartridge 403 into chassis 402 by engagement of valves 408A and 408B with actuators attached to chassis 402.

Figure 12:
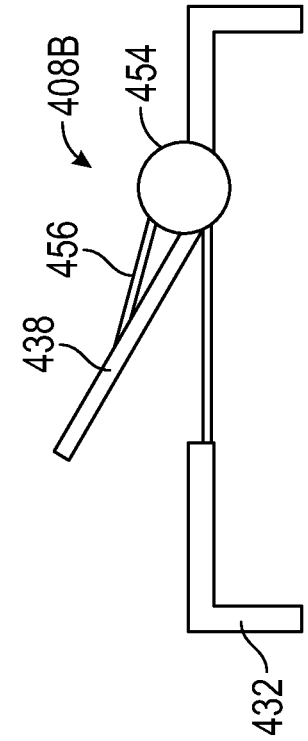
FIGS. 12, 13 and 14 comprise schematic illustrations of a spring valve, a pressure valve and a motorized valve suitable for use as the valve of FIG. 11.

In examples, valves 408A and 408B can be attached to chassis 402 and can be configured to open upon insertion of cartridge 403 into chassis 402 by engagement of valves 408A and 408B with actuators attached to cartridge 402, as shown in FIG. 12.

Figure 10:
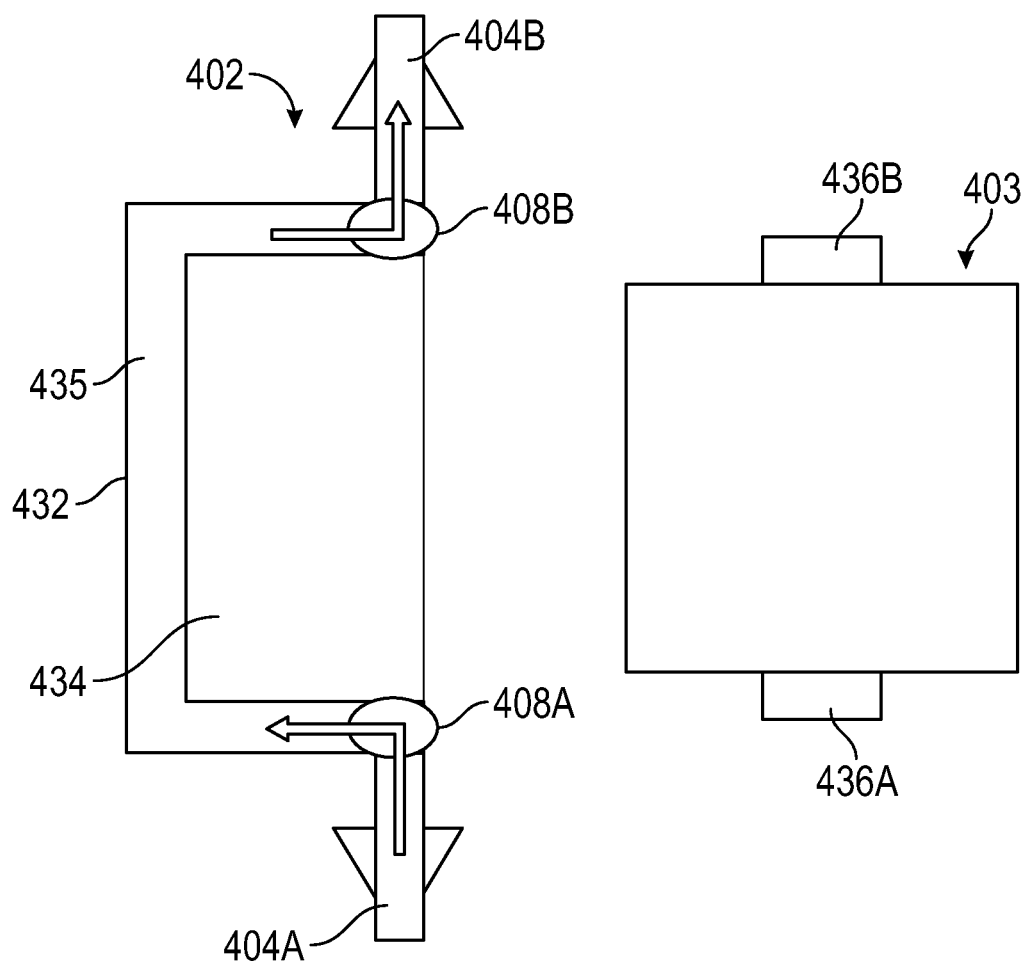
FIG. 10 is a schematic cross-sectional view of the chassis of FIG. 9 with the cartridge removed.

FIG. 10 is a schematic cross-sectional view of chassis 402 of FIG. 9 with cartridge 403 removed. Chassis 402 can be configured as a body to easily receive cartridge 403 to permit flow through cartridge 403 when cartridge 403 is seated within chassis 402, and to allow flow around the space for cartridge 430 when cartridge 403 is removed from chassis 402. Chassis 402 can comprise shell 432 having socket 432, internal passage 434, as well as valves 408A and 408B. Cartridge 403 can comprise actuators 436A and 436B. In an example, chassis 402 can comprise a half cylinder.

When cartridge 403 is not located in socket 432, valves 408A and 408B can be configured to direct flow from stem 404A, through valve 408A, through internal passage 435, through valve 408B and into stem 404B. When cartridge 403 is positioned in socket 432, valves 408A and 408B can be configured to direct flow from stem 404A, through valve 408A, through cartridge 403, through valve 408B and into stem 404B.

Figure 11:
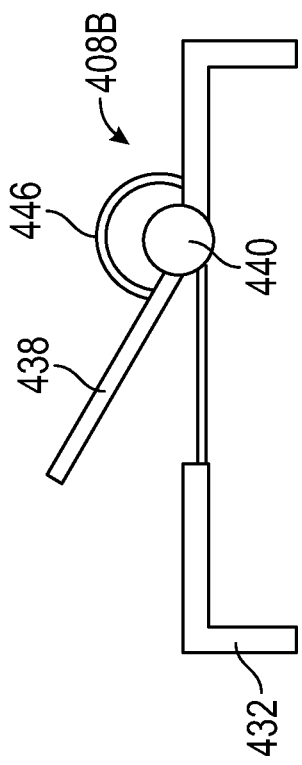
FIG. 11 is a schematic cross-sectional view of a valve of the chassis of FIG. 9 configured to interact with an actuator of the cartridge.
Figure 13:
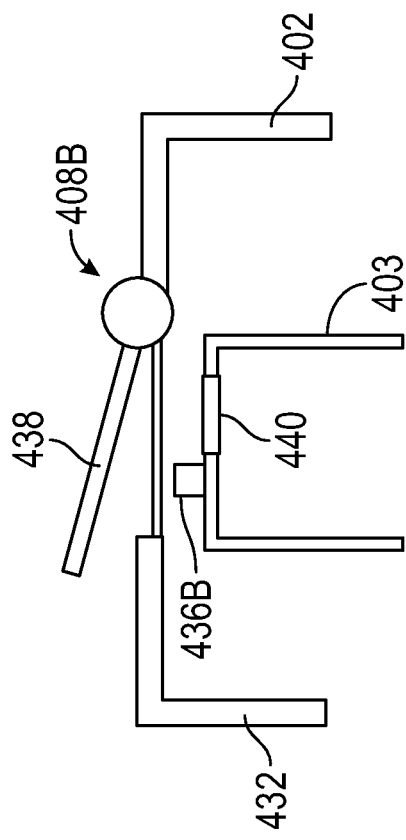
Figure 14:
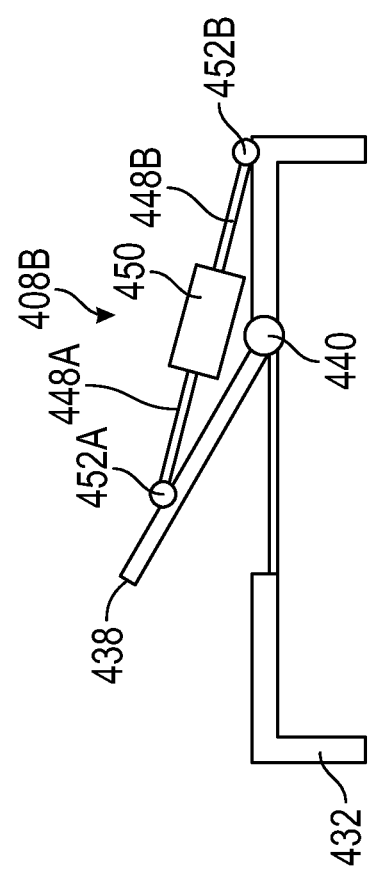

FIG. 11 is a schematic cross-sectional view of a valve 408B of chassis 402 configured to interact with actuator 436B of cartridge 403. Valve 408B can comprise flap 438 and hinge 440. As shown in FIGS. 12-14, flap 438 can be biased toward shell 432. Cartridge 403 can be fit into socket 432 of chassis 402 such that actuator 436B pushes against valve 408B. Actuator 436B can overcome bias applied to flap 438 by a biasing device. Thus, flow can be permitted through valve 408B from within cartridge 403. When flap 438 is closed, fluid can flow freely from internal passage 435 to stem 404B. When flap 438 is opened, flap 438 can close off internal passage 435 such that fluid can flow freely from cartridge 403 to stem 404B.

FIGS. 12, 13 and 14 comprise schematic illustrations of spring valve 440, pressure valve 442 and motorized valve 444 suitable for use as valve 408B of FIG. 11.

As shown in FIG. 12, spring valve 440 can comprise flap 438 connected to shell 432 at hinge 440, with flap 438 being biased by spring 446. Spring 446 can be configured to push flap 438 against chassis 402 to close off flow through cartridge 403 and permit flow through internal passage 435. Actuator 436B can be configured to engage flap 438 to push flap 438 away from chassis 402.

As shown in FIG. 13, pressure valve 442 can comprise rod 448A, dashpot 450 and rod 448B. Rod 448A can be attached to flap 438 at hinge 452A and rod 448B can be attached to shell 432 at hinge 452B. Dashpot 450 can be configured to push flap 438 against chassis 402 to close off flow through cartridge 403 and permit flow through internal passage 435. Actuator 436B can be configured to engage flap 438 to push flap 438 away from chassis 402.

As shown in FIG. 14, motorized valve 444 can comprise motor 454, which can be connected to flap 438 via linkage 456. In additional examples, motor 454 can act as hinge 440 and can be directly coupled to flap 438. Motor 454 can be configured to push flap 438 against chassis 402 to close off flow through cartridge 403 and permit flow through internal passage 435. Actuator 436B can be configured to engage flap 438 to push flap 438 away from chassis 402.

FIG. 15 is a schematic cross-sectional view of stone fragment capture system 500 for use with stone fragmentation system 252, as well as other systems described herein. Stone fragmentation system 252 can comprise any of the lithotripsy systems described herein and can comprise handle 204 and shaft 206. Stone fragment capture system 500 can comprise stone capture device 502 with vacuum port 504. Stone capture device 502 can comprise housing 506 comprising upper component 508A and lower component 508B, and coupler 510. FIG. 16 is a schematic top view of stone capture device 502 of FIG. 15 showing a position of tube connector 512 relative to coupler 510. FIGS. 15 and 16 are discussed concurrently.

Stone fragment capture system 500 can comprise a system for catching stone fragments that simultaneously allows for access to the interior of handle 204 and shaft 206 via vacuum port 504. Vacuum port 504 can comprise a sealable port that can be opened to allow for insertion of an instrument into handle 204 through stone capture device 502. In examples, the sealable port can comprise a threaded port having a cap. In additional examples, the sealable port can comprise a self-sealing access point, such as an iris point entry system comprising a plurality of deflectable tabs that can abut or overlap each other in a non-deflected state to seal off an access point, but that can be bent or deflected away from each other to allow entry into the access point.

Vacuum port 504 and coupler 510 can be aligned along axis A6 of hand-held probe 202, along which shaft 206 and handle 204 extend. As such in the event of a blockage within handle 204 or shaft 206, such as from a lodged stone fragment, a probe can be inserted into vacuum port 504 all the way toward distal tip 216 (FIG. 17) of shaft 206 to push or otherwise dislodge the stone fragment or other obstruction.

Stone capture device 500 can function similarly to container 258 of FIG. 3, container 308 of FIG. 5 or any of the other stone fragment captures systems described or contemplated herein. However, as shown in FIG. 16, tube connector 512 can be positioned off of axis A6 along axis A7 to allow for vacuum port 504 to be axially aligned with coupler 510. Vacuum port 504 can be integrated into container 258 of FIG. 3 and container 308 of FIG. 5 by offsetting outlet port 266 and outlet 316 from inlet port 264 and inlet 314, respectively. For example, with reference to FIG. 3, outlet port 266 can be offset from axis A3 on 282 on end plate 282 closer to the sidewall of cap 262 to allow for positioning of an entry port, such as vacuum port 504, to align with inlet port 264. In such case, valve 254 can be omitted or can be configured as a two-way valve to allow flow in both direction when activated (e.g., sucked open by a vacuum to allow flow out or pushed open by a probe to allow clearance of a blockage). Similarly, chassis 402 of FIG. 10 can be modified accordingly to include a vacuum port.

Upper component 508A and lower component 508B can be releasably coupled to each other to allow for access to stone fragments captured therein. For example, upper component 508A and lower component 508B can be threadedly connected or can be connected by a snap-fit feature. Furthermore, a sealing member, such as an O-ring seal can be provided between upper component 508A and lower component 508B.

Figure 17:
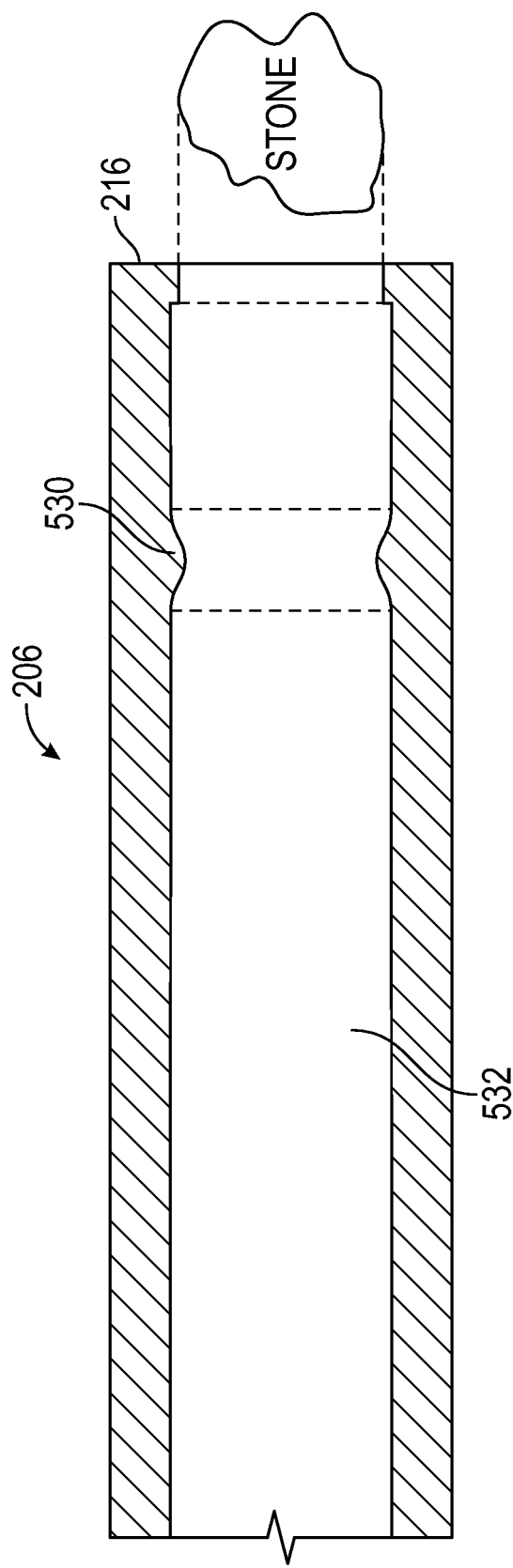
FIG. 17 is a schematic cross-sectional view of a distal tip of the probe of FIG. 2 showing a flow restriction configured to size-limit entry of stones into the probe.

FIG. 17 is a schematic cross-sectional view of distal end 216 of shaft 206 of FIG. 2 showing a flow restriction 530 located in lumen 532 configured to size-limit entry of stones into shaft 206. Flow restriction 530 can comprise a narrowing of lumen 532 by a ring-like or annular feature. Flow restriction 530 can define a maximize stone size that can be permitted through shaft 206, which can be a stone size that is smaller than the narrowest passage through shaft 206 and handle 204, thereby reducing the chances of a blockage forming in hand-held probe 202. In examples, the inner diameter of flow restriction 530 can be larger than the maximum sized stone fragment desired to be collected in the stone fragment capture devices of the present disclosure.

Figure 18:
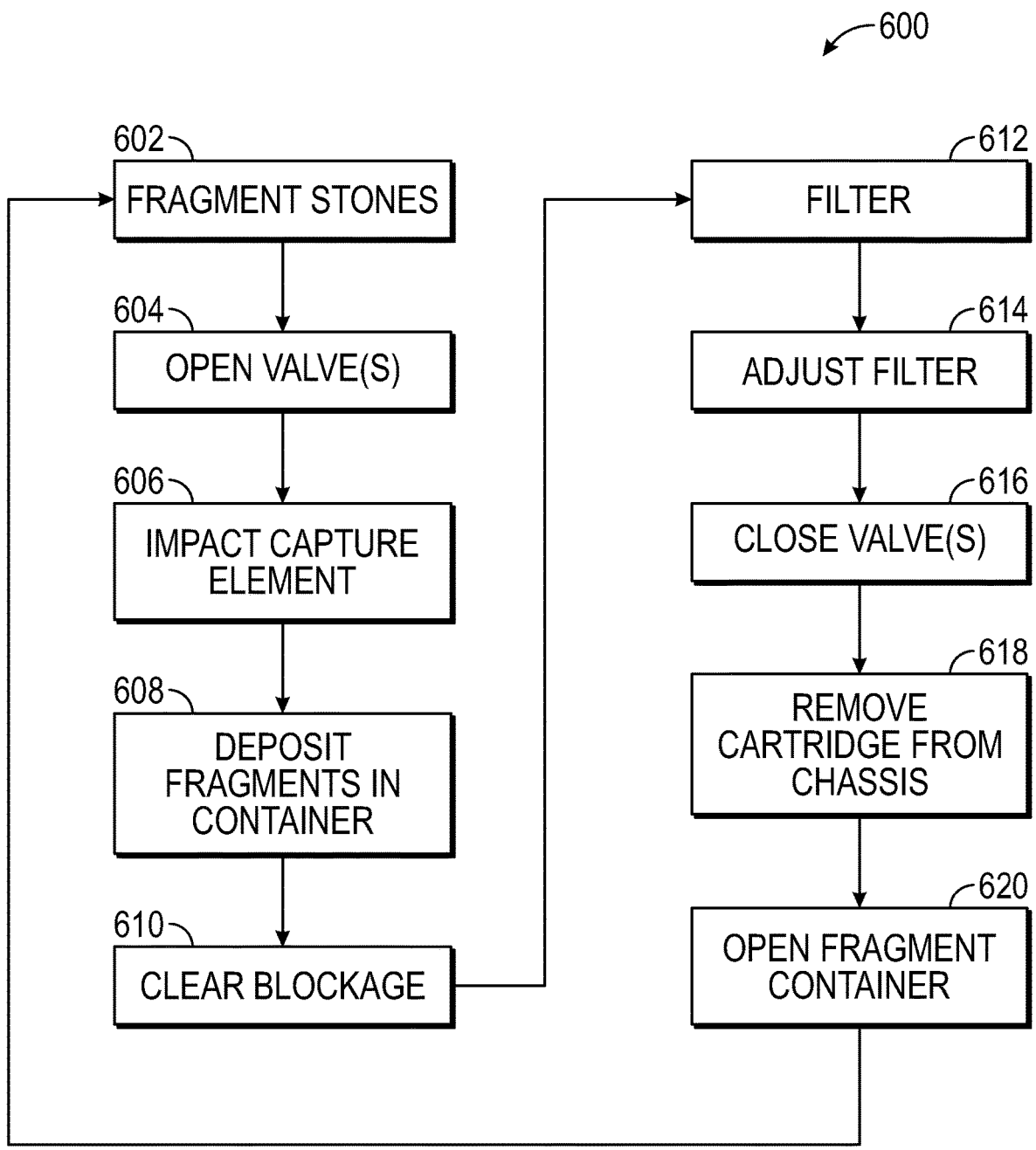
FIG. 18 is a flow chart illustrating a method for retrieving stone fragments from a lithotripsy procedure using the devices and stone fragment capture systems of the present disclosure.

FIG. 18 is a line diagram illustrating method 600 for retrieving stone fragments from a lithotripsy procedure using the devices and stone fragment capture systems of the present disclosure. Method 600 illustrates various exemplary steps of a stone fragment recovery process. Other steps as described herein can be included and some steps can be omitted. Additionally, the illustrated steps can be performed in a different order.

At step 602, stones within a patient can be fragmented using a surgical device, such as one of the lithotripsy devices disclosed herein, e.g., lithotripter 102 and hand-held probe 202.

At step 604, valves, such as an inlet valve (e.g., valve 254, valve 304), of a stone fragment capture device can be opened, such as by the drawing of a vacuum through the medical device used in step 602, At step 606, a stone fragment being pulled by the vacuum being drawn through the stone fragment capture device can impact a capture element, such as a tapered tube (e.g., inlet port 264), a filter (e.g., filter 256, filter 306), a valve (e.g., valve 254, valve 304), an orifice (e.g., flow restricting valve 360) or a baffle (e.g., baffle 267), within the stone fragment capture device.

At step 608, the stone fragment can be diverted out of a main flow of fluid through the stone fragment capture device to be deposited within a container (e.g., container 258, container 308) of the stone fragment capture device.

At step 610, a blockage, if any, can be cleared from the surgical device, such as by extending a probe into the stone fragment capture device through a vacuum port (e.g., vacuum port 504), through the stone fragment capture device and into a shaft of the surgical device to clear the blockage.

At step 612, biological matter flowing through the stone fragment capture device can impact a filter (e.g., filter 256, filter 306) within the stone fragment capture device, thereby only allowing liquid and sufficiently small solids to pass therethrough.

At step 614, a size of filtering capacity of the filter can be adjusted (e.g., by rotating handle 358 or handle 366) to control the size of debris retained in the stone fragment capture device.

At step 616, valves, such as an outlet valve (e.g., flow restricting valve 360, valve 408B), of the stone fragment capture device can be closed to retain stone fragments deposited therein.

At step 618, a cartridge (e.g., cartridge 403) of the stone fragment capture device holding the stone fragments can be removed from a chassis (e.g., chassis 402) securing the stone fragment capture device to the surgical device.

At step 620, the cartridge or other container holding the stone fragments can be opened (e.g., by removing cap 262 or cap 312 or separating components 508A and 508B) such that the stone fragments can be accessed, such as for analysis.

VARIOUS NOTES AND EXAMPLES

For the purposes of this disclosure, "proximal" refers to an end of the system that is closer the device operator during use, and "distal" refers to an end of the system that is distal, or further from the device operator during use.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Example 1 is a lithotripsy device comprising: a handpiece; a lithotripsy probe extending from the handpiece; an energization source coupled to the handpiece configured to deliver an energy to a distal end of the lithotripsy probe; a suction passage extending from the distal end of the probe and through the handpiece; and a capture device coupled to the handpiece, the capture device comprising: a container comprising: a wall defining a storage space within the container; an entry port configured to couple to the handpiece at the suction passage; and an exit port; and a capture element connected to the container and configured to facilitate capture of stone fragments within the storage space.

In Example 2, the subject matter of Example 1 includes, wherein the capture element comprises a filter disposed in the container and extending across the exit port.

In Example 3, the subject matter of Example 2 includes, wherein the container comprises a first portion having the entry port and a second portion having the exit port, wherein the first and second portions are separable to be able to access the storage space.

In Example 4, the subject matter of Example 3 includes, wherein the filter is coupled to the second portion.

In Example 5, the subject matter of Examples 2-4 includes, wherein the filter is adjustable.

In Example 6, the subject matter of Examples 2-5 includes, wherein the filter comprises an iris valve.

In Example 7, the subject matter of Examples 2-6 includes, wherein the filter comprises first and second mesh screens, wherein the first mesh screen is rotatably adjustable relative to the second mesh screen.

In Example 8, the subject matter of Examples 1-7 includes, wherein the capture element comprises a baffle disposed between the inlet port and the exit port.

In Example 9, the subject matter of Examples 1-8 includes, wherein the capture element comprises an elongate tube extending from the entry port.

In Example 10, the subject matter of Examples 1-9 includes, a first sealing element disposed at the entry port.

In Example 11, the subject matter of Example 10 includes, wherein the first sealing element comprises a flapper valve or a sliding valve.

In Example 12, the subject matter of Example 11 includes, wherein the first sealing element is biased to a closed position.

In Example 13, the subject matter of Examples 10-12 includes, a second sealing element located at an outlet of the container.

In Example 14, the subject matter of Example 13 includes, a chassis, wherein the container is removable from the chassis and the second sealing element is located at the exit port.

In Example 15, the subject matter of Example 14 includes, wherein the chassis comprises: a seat for receiving the container; and a bypass suction passage circumventing the seat.

In Example 16, the subject matter of Examples 13-15 includes, wherein the second sealing element comprises a vacuum port.

In Example 17, the subject matter of Example 16 includes, wherein the vacuum port is axially aligned with the suction passage extending from the distal end of the probe and through the handpiece.

In Example 18, the subject matter of Examples 16-17 includes, wherein the vacuum port is axially aligned with the entry port of the container and the exit port of the container is offset from the vacuum port and the entry port.

In Example 19, the subject matter of Examples 17-18 includes, wherein the vacuum port comprises a self-sealing valve.

In Example 20, the subject matter of Examples 1-19 includes, a tube connecting the inlet port with the handpiece.

Example 21 is a method of retrieving stone fragments from a lithotripsy procedure, the method comprising: fragmenting stones with a lithotripsy device; drawing a vacuum through the lithotripsy device to pull stone fragments and waste fluid through the lithotripsy device; pulling the vacuum through a stone capture device connected to the lithotripsy device; depositing stone fragments within the stone capture device using a capture element; and continuing to draw the vacuum to deposit the waste fluid in a waste container.

In Example 22, the subject matter of Example 21 includes, guiding the stones into the capture element of the stone capture device to deposit the stone fragments within the stone capture device.

In Example 23, the subject matter of Example 22 includes, wherein the capture element comprises a baffle.

In Example 24, the subject matter of Examples 21-23 includes, filtering the stone fragments from the waste fluid within the stone capture device.

In Example 25, the subject matter of Example 24 includes, adjusting a filtering capability of the filter.

In Example 26, the subject matter of Examples 21-25 includes, opening a valve with the stone capture device to permit the stone fragments and waste fluid into the stone capture device.

In Example 27, the subject matter of Examples 21-26 includes, adjusting an orifice size of the stone capture device to control egress of stone fragments from the stone capture device.

In Example 28, the subject matter of Examples 21-27 includes, opening the stone capture device to access deposited stone fragments.

In Example 29, the subject matter of Examples 21-28 includes, removing the stone capture device from a chassis coupling the stone capture device to the lithotripsy device.

In Example 30, the subject matter of Examples 21-29 includes, inserting a probe through a vacuum port on the stone capture device and into the lithotripsy device to clear a blockage in the lithotripsy device.

Example 31 is a capture device for collecting fragments generated during lithotripsy, the capture device comprising: a container comprising: a wall defining a storage space within the container; an entry port coupled to the wall and configured to couple to the handpiece at the suction passage; and an exit port coupled to the wall; a capture element connected to the container and configured to facilitate capture of stone fragments within the storage space; and a coupler for connecting the container to a handpiece of a lithotripsy device.

In Example 32, the subject matter of Example 31 includes, wherein the coupler element comprises a barbed hose coupler.

In Example 33, the subject matter of Examples 31-32 includes, wherein the coupler element comprises a resilient opening extending through the wall.

In Example 34, the subject matter of Examples 31-33 includes, wherein the exit port comprises a barbed hose coupler.

In Example 35, the subject matter of Examples 31-34 includes, wherein the capture element comprises an adjustable filter.

In Example 36, the subject matter of Examples 31-35 includes, wherein the capture element comprises an adjustable orifice.

In Example 37, the subject matter of Examples 31-36 includes, wherein the capture element comprises an elongate tube extending from the entry port.

In Example 38, the subject matter of Examples 31-37 includes, wherein the capture element comprises a baffle.

In Example 39, the subject matter of Examples 31-38 includes, a first sealing element disposed at the entry port.

In Example 40, the subject matter of Examples 31-39 includes, a second sealing element located at an outlet of the container.

In Example 41, the subject matter of Example 40 includes, a chassis, wherein the container is removable from the chassis and the second sealing element is located at the exit port.

In Example 42, the subject matter of Examples 40-41 includes, wherein the second sealing element comprises a vacuum port axially aligned with the entry port, the vacuum port comprising a self-sealing valve.

Example 43 is at least one machine-readable medium including instructions that, when executed by processing circuitry, cause the processing circuitry to perform operations to implement of any of Examples 1-42.

Example 44 is an apparatus comprising means to implement of any of Examples 1-42.

Example 45 is a system to implement of any of Examples 1-42.

Example 46 is a method to implement of any of Examples 1-42.

Each of these non-limiting examples can stand on its own, or can be combined in various permutations or combinations with one or more of the other examples.

What is claimed is:

1. A lithotripsy device comprising:
    a handpiece comprising a distal end portion and a proximal end portion, wherein the handpiece further comprises:
        an elongate body;
        a first end face at the distal end portion;
        a second end face at the proximal end portion;
        a first control feature positioned on the elongate body; and
        a second control feature positioned on the elongate body;
    a lithotripsy probe extending from the first end face of the distal end portion of the handpiece, wherein the first control feature is configured to control activation energy for the lithotripsy probe;
    a suction passage extending through the lithotripsy probe and through the handpiece, wherein the second control feature is configured to control suction through the suction passage; and
    a capture device coupled directly to the handpiece to receive stone fragments from the suction passage, the capture device comprising:
        a container comprising:
            a wall defining a storage space within the container;
            an entry port configured to couple to the handpiece at the suction passage; and
            an exit port;
        wherein the container of the capture device couples directly to the second end face; and
        a capture element is connected to the container and is configured to facilitate capture of the stone fragments within the storage space.

2. The lithotripsy device of claim 1, wherein the capture device is releasably attached to the handpiece via an attachment mechanism.

3. The lithotripsy device of claim 2, wherein the attachment mechanism comprises:
    a hose coupler extending from the proximal end portion of the handpiece, wherein the suction passage extends through the hose coupler; and
    a socket at the entry port to receive the hose coupler.

4. The lithotripsy device of claim 3, wherein the hose coupler comprises a stem having a barb.

5. The lithotripsy device of claim 4, wherein the socket for the container comprises a tube extending into the storage space within the wall.

6. The lithotripsy device of claim 5, wherein the tube is tapered to slow the stone fragments entering the storage space.

7. The lithotripsy device of claim 5, wherein the barb comprises a resilient rim extending around the stem, wherein a diameter of the barb is larger than an inner diameter of the tube.

8. The lithotripsy device of claim 1, further comprising an elongate flexible tube integral with the exit port.

9. The lithotripsy device of claim 1, wherein the container of the capture device abuts the handpiece of the lithotripsy device.

10. The lithotripsy device of claim 9, wherein:
the entry port is located in a floor of the container connected to the wall; and
the handpiece has a proximal-most end wall into which the suction passage extends;
wherein the floor abuts the proximal-most end wall.

11. The lithotripsy device of claim 1, wherein:
the first control feature comprises a first button; and
the second control feature comprises a suction knob.

12. The lithotripsy device of claim 1, wherein the capture element comprises a filter disposed in the container to filter fluid flowing into the exit port.

13. The lithotripsy device of claim 12, wherein the capture element further comprises a deflector positioned within the storage space to deflect the stone fragments away from the exit port.

14. The lithotripsy device of claim 1, wherein the capture element comprises a valve disposed at the entry port, wherein:
the valve is biased to a closed position; and
the valve is configured to be opened when coupled to the handpiece.

15. The lithotripsy device of claim 1, wherein the container comprises a first portion and a second portion, wherein the first portion and the second portion are separable to be able to access the storage space.

16. The lithotripsy device of claim 1, further comprising an energization source coupled to the handpiece configured to deliver an energy to a distal end of the lithotripsy probe.

17. An in-line capture device for collecting stone fragments generated during a lithotripsy procedure from a handpiece of a lithotripsy device, the in-line capture device comprising:
a container comprising:
a wall defining a storage space within the container;
a first entry port coupled to the wall at a floor; and
a first exit port coupled to the wall;
a capture element connected to the container and configured to facilitate capture of stone fragments within the storage space; and
a first coupler on the floor at the first entry port configured to connect the container to a second coupler of the handpiece of the lithotripsy device such that the handpiece abuts the floor, and a second coupler of the handpiece is within the container.

18. The in-line capture device of claim 17, wherein the first coupler comprises a resilient opening extending through the container.

19. The in-line capture device of claim 17, wherein the first coupler comprises an elongate tube extending from the floor at the first entry port along a first axis to extend into the storage space, wherein the first axis of the elongate tube coaxially aligns with a second axis of the first exit port.

20. The in-line capture device of claim 19, wherein the capture element comprises a deflector positioned within the storage space between the first entry port and the first exit port to deflect the stone fragments away from the first exit port, wherein the deflector is angled obliquely relative to an axis extending between the first entry port and the first exit port.

21. The in-line capture device of claim 17, wherein the first coupler is configured to receive a barbed hose coupler comprising the second coupler.

22. The in-line capture device of claim 17, wherein the capture element comprises a first sealing element disposed at the first entry port.

23. The in-line capture device of claim 17, wherein the capture element comprises a filter disposed within the storage space.

24. The in-line capture device of claim 17, wherein the container further comprises:
an end plate connected to the wall into which the first exit port extends;
wherein the end plate is removable from the wall to access the storage space.

25. A lithotripsy device comprising:
a handpiece comprising a distal end portion and a proximal end portion;
a lithotripsy probe extending from the distal end portion of the handpiece;
a suction passage extending through the lithotripsy probe and through the handpiece; and
a capture device coupled directly to the handpiece to receive stone fragments from the suction passage, the capture device comprising:
a container comprising:
a wall defining a storage space within the container;
an entry port configured to couple to the handpiece at the suction passage; and
an exit port; and
a capture element connected to the container and configured to facilitate capture of the stone fragments within the storage space;
wherein the container of the capture device abuts the handpiece of the lithotripsy device.

26. A method of retrieving stone fragments during a lithotripsy procedure, the method comprising:
fragmenting stones with a lithotripsy device, the lithotripsy device comprising a handpiece having a coupler extending from an exit port;
drawing a vacuum through the lithotripsy device to pull the stone fragments and waste fluid through the lithotripsy device;
pulling the vacuum through a stone capture device directly connected to the lithotripsy device, wherein the stone capture device abuts the handpiece at the exit port so that the coupler extends into the stone capture device;
depositing the stone fragments within the stone capture device using a capture element; and
continuing to draw the vacuum to deposit the waste fluid in a waste container.

27. The method of claim 26, wherein depositing the stone fragments within the stone capture device using the capture element comprises:
guiding the stones fragments out of the lithotripsy device and into the stone capture device through a coupling interface between the lithotripsy device and the stone capture device.

28. The method of claim 27, wherein guiding the stones fragments out of the lithotripsy device and into the stone capture device through the coupling interface between the lithotripsy device and the stone capture device comprises:
guiding the stone fragments through a tube stem of the lithotripsy device; and
guiding the stone fragments from the tube stem through an entry port in the stone capture device that receives the tube stem.

29. The method of claim 26, wherein depositing the stone fragments within the stone capture device using the capture element comprises:
   opening a valve with the stone capture device by coupling of the stone capture device to the lithotripsy device to permit entry of the stone fragments and the waste fluid into the stone capture device.

30. The method of claim 26, wherein depositing the stone fragments within the stone capture device using the capture element comprises:
   filtering the stone fragments from the waste fluid within the stone capture device.

31. The method of claim 26, wherein depositing the stone fragments within the stone capture device using the capture element comprises:
   deflecting the stone fragments entering the stone capture device to discourage egress of the stone fragments out of the stone capture device.

32. The method of claim 26, wherein a first axis of an inlet of the stone capture device coaxially aligns with a second axis of an outlet of the stone capture device.

* * * * *